US010869942B2

(12) United States Patent
Olberg et al.

(10) Patent No.: US 10,869,942 B2
(45) Date of Patent: Dec. 22, 2020

(54) METHOD

(71) Applicant: Norsk Medisinsk Syklotronsenter AS, Oslo (NO)

(72) Inventors: Dag Erlend Olberg, Oslo (NO); Anders Svadberg, Oslo (NO)

(73) Assignee: Norsk Medisinsk Syklotronsenter AS, Oslo (NO)

( * ) Notice: Subject to any disclaimer, the term of this patent is extended or adjusted under 35 U.S.C. 154(b) by 0 days.

(21) Appl. No.: 15/771,152

(22) PCT Filed: Oct. 26, 2016

(86) PCT No.: PCT/EP2016/075868
§ 371 (c)(1),
(2) Date: Apr. 26, 2018

(87) PCT Pub. No.: WO2017/072200
PCT Pub. Date: May 4, 2017

(65) Prior Publication Data
US 2018/0311384 A1 Nov. 1, 2018

(30) Foreign Application Priority Data

Oct. 26, 2015 (GB) .................................. 1518918.6

(51) Int. Cl.
| | |
|---|---|
| A61K 51/00 | (2006.01) |
| A61M 36/14 | (2006.01) |
| A61K 51/04 | (2006.01) |
| C07D 213/80 | (2006.01) |
| C07D 213/803 | (2006.01) |
| C07B 59/00 | (2006.01) |
| C07D 213/61 | (2006.01) |
| C07D 213/74 | (2006.01) |
| A61K 51/08 | (2006.01) |
| C07D 213/65 | (2006.01) |
| C07D 213/82 | (2006.01) |
| C07D 401/04 | (2006.01) |

(52) U.S. Cl.
CPC ...... *A61K 51/0455* (2013.01); *A61K 51/0497* (2013.01); *A61K 51/088* (2013.01); *C07B 59/002* (2013.01); *C07B 59/008* (2013.01); *C07D 213/61* (2013.01); *C07D 213/65* (2013.01); *C07D 213/74* (2013.01); *C07D 213/80* (2013.01); *C07D 213/803* (2013.01); *C07D 213/82* (2013.01); *C07D 401/04* (2013.01)

(58) Field of Classification Search
CPC ............ A61K 51/0455; A61K 51/0497; A61K 51/088; C01D 213/803
USPC ...................................................... 424/1.89
See application file for complete search history.

(56) References Cited

U.S. PATENT DOCUMENTS

| 5,436,325 A * | 7/1995 | Johnson | ................... C07H 5/02 |
|---|---|---|---|
| | | | 536/18.4 |
| 8,686,002 B2 | 4/2014 | Amberg et al. | |
| 2008/0095701 A1* | 4/2008 | Solbakken | ........... A61K 51/088 |
| | | | 424/1.89 |

FOREIGN PATENT DOCUMENTS

| WO | WO-2008128306 A1 * | 10/2008 | ............... C01B 9/08 |
|---|---|---|---|
| WO | 2010114723 A1 | 10/2010 | |
| WO | 2014020035 A1 | 2/2014 | |
| WO | 2016030329 A1 | 3/2016 | |
| WO | 2016062370 A1 | 4/2016 | |

OTHER PUBLICATIONS

Zhang et al. J. Alzh. Dls. 31 (2012) 60-612.*
Mulholland et al. J. Labeled Compd Radiopharm. 1989, 378-380. (Year: 1989).*
Search Report under Section 17 issued in Great Britain Application No. GB1518918.6, dated Aug. 24, 2016.
Notification of the International Search Report and Written Opinion issued in PCT/EP2016/075868, dated Jan. 12, 2017.
Chen, et al. 2-(3-(1-Carboxy-5-[(6-[18F]Fluoro-Pyridine-3-Carbonyl)-Amino]-Pentyl}-Ureido)-Pentanedioic Acid, [18F DCFPyL,a PSMA-Based PET Imaging Agent for Prostate Cancer. Oct. 31, 2011. Clinical Cancer Research. pp. 7645-7653.
Ermert. F-Labelled Intermediates for Radiosynthesis by Modular Build-Up Reactions: Newer Developments. Mar. 27, 2014. Hindawi Publishing Corporation BioMed Research International vol. 2014, Article ID 812973, 15 pages.
Greguric, et al. Discovery of [18F]N-(2-(Diethylamino)ethyl)-6-fluoronicotinamide: A Melanoma Positron Emission Tomography Imaging Radiotracer with High Tumor to Body Contrast Ratio and Rapid Renal Clearance. Jun. 10, 2009. J. Med. Chem. 2009, 52, 5299-5302.
Mulholland, et al. Polymer-Supported Nucleophilic Radiolabeling Reactions With [ 18F] Fluoride and [11 C] Cyanide Ion on Quaternary Ammonium Resins. Division of Nuclear Medicine, University of Michigan, Ann Arbor, MI 48109. 3 pages.
Kugler, et al. Evaluation of 18F-Labeled Benzodioxine Piperazine-Based Dopamine D4 Receptor Ligands: Lipophilicity as a Determinate of Nonspecific Binding. J. Med. Chem. 2011, 54, 8343-8352.
Malik, et al. Radiosynthesis of a new PSMA targeting ligand {[18F]FPy-DUPA-Pep}. Jan. 11, 2011. Clinic for Nuclear Medicine, University Hospital. Applied Radiation and Isotopes 69 1014-1018.

(Continued)

Primary Examiner — Michael G. Hartley
Assistant Examiner — Sean R Donohue
(74) Attorney, Agent, or Firm — Meunier Carlin & Curfman LLC

(57) ABSTRACT

The present invention relates to new and improved methods of synthesizing radiolabelling agents which can be used to label biomolecules for use as radiopharmaceuticals. It further relates to certain novel radiolabelling agents and their use in such methods. PET imaging methods and methods of diagnosis employing such radiolabelling agents form a further aspect of the invention.

16 Claims, 2 Drawing Sheets

(56) References Cited

OTHER PUBLICATIONS

Mathiessen, et al. Automated Solid-Phase Radiofluorination Using Polymer-Supported Phosphazenes. Aug. 30, 2013. Molecules 2013, 18, 10531-10547.

Olberg, et al. One Step Radiosynthesis of 6-[18F]Fluoronicotinic Acid 2,3,5,6-Tetrafluorophenyl Ester ([18F]F—Py—TFP): A New Prosthetic Group for Efficient Labeling of Biomolecules with Fluorine-18. Oct. 26, 2009. J. Med. Chem. 2010, 53, 1732-1740.

Richter, et al. 18F-Labeled Peptides: The Future Is Bright. Oct. 22, 2014. Molecules 2014, 19, 20536-20556.

Tang, et al. Fully automated synthesis of 0-(3-[18F]fluoropropyl)L-tyrosine by direct nucleophilic exchange on a quaternary 4-aminopyridinium resin. Nov. 27, 2002. Applied Radiation and Isotopes 58 (2003) 685-689.

Toorongian, et al. Routine Production of 2-Deoxy-2-[18F]fluoro-D-glucose by Direct Nucleophilic Exchange on a Quarternary 4-Aminopyridinium Resin. 1990. International Journal of Radiation Applications and Instrumentation Part B: Nuclear Med. Biol. vol. 17, No. 3. pp. 273-279.

Mathiessen, et al. Towards automated solid phase radiofluorination for dose-on-demand PET: retention of activity by solid support. Feb. 25, 2014. Radiochim. Acta 2015; 103(3): 227-232.

Basuli, et al. Facile room terperature synthesis of fluorine-18 labeled fluoronicotinic acid-2,3,5,6-tetrafluorophyenyl ester without azeotropic drying of fluorine-18. Nuclear Medicine and biology 43 (2016). pp. 770-772.

Wilhelm; Amberg et al., "Preparation of 2-aminoquinolines and related compounds 5-ht5 receptor inhibitors," CAPLUS, Jan. 1, 2007.

* cited by examiner

METHOD

The present invention relates to new and improved methods of synthesizing radiolabelling agents which can be used to label biomolecules for use as radiopharmaceuticals. It further relates to certain novel radiolabelling agents and their use in such methods.

The method of the invention is simpler, faster and higher yielding than conventional methods for preparing radiolabelling agents, can be carried out at room temperature, and does not require a phase-transfer catalyst. The radiolabelled compounds produced by the method find particular use as labelling agents (prosthetic groups), for example in the radiolabelling of biomolecules or other molecules which cannot be labelled directly (or can only be labelled in poor yield) by nucleophilic addition of a radionuclide or which otherwise require the use of reaction mixtures which do not allow easy separation of the labelled product and nonlabelled biomolecule. Radiolabelled compounds obtained by the method of the invention and biomolecules labelled with such compounds find particular application as tracers in positron emission tomography (PET). Advantageously, the method of the invention can be performed on existing commercial PET synthesizer platforms.

PET is an imaging modality increasingly used in nuclear medicine. Fluorine-18 ($^{18}$F) has near-ideal properties for PET imaging due to its half-life of 110 minutes, high positron abundance (97%), low positron energy (0.634 MeV) and its high production efficiency using a cyclotron.

2-[$^{18}$F]fluoro-2-deoxy-D-glucose (FDG) is by far the most-used $^{18}$F PET tracer in a clinical setting. However, there are several indications where FDG shows no utility or has low impact on clinical management. Other tracers are therefore needed to fill this void. One class of tracers is based on biomolecules (e.g. peptides, peptidomimetics, affibodies, diabodies, nanobodies, dendrimers, aptamers, antibodies, antibody mimetics and proteins). This class of tracers is increasingly finding use in nuclear medicine. Peptides and other biomolecules are excellent targeting probes (tracers) for PET due to their high specificity. Their biological pharmacokinetics are also well-matched to the radioactive half-life of $^{18}$F, especially in the case of peptides and peptidomimetics. Examples of such tracers include prostate specific antigen membrane antigen (PSMA), somatostatin analogues and chemokine receptor targeting probes. Examples of biomolecule-based tracers are described in Chen et al., Clinical Cancer Research, 17(24): 7645-53, (2011); and in Greguric et al., Journal of Medicinal Chemistry, 52: 5299-5302 (2009).

The chemistry of $^{18}$F in relation to biomolecules is hampered by the harsh conditions required to form a covalent bond of $^{18}$F to the biomolecule. As a consequence, $^{18}$F is normally introduced into biomolecules using an $^{18}$F-prosthetic group. Several $^{18}$F-based prosthetic groups have been described in the literature. However, these suffer from complicated multi-step synthetic routes and protracted synthesis times, often 90 minutes or more. This has hindered the widespread use of $^{18}$F-labelled biomolecules in PET. Instead, there is increasing clinical use of $^{68}$Ga-labelled peptides such as [$^{68}$Ga]DOTATOC and [$^{68}$Ga]PSMA, despite the fact that $^{68}$Ga is costlier to produce and has a sub-optimal half-life and sub-optimal imaging properties compared to $^{18}$F.

To allow a more widespread clinical use of $^{18}$F-based biomolecules, a simplified and high-yielding process for their production is required. This in turn requires a simpler, more cost-effective process for producing the required $^{18}$F-prosthetic groups in high yield.

An $^{18}$F-prosthetic group suitable for labelling biomolecules is [$^{18}$F]fluoronicotinic acid 2,3,5,6-tetrafluorophenyl ester (abbreviated as [$^{18}$F]F-Py-TFP). This has the following structure:

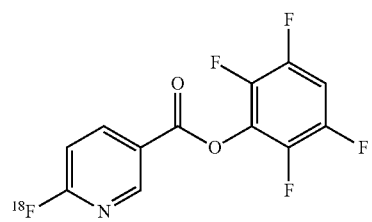 [SMILES: O=C(Oc1c(F)c(F)cc(F)c1F)c1ccc([18F])nc1]

[$^{18}$F]F-Py-TFP can be synthesised by reacting [$^{18}$F]fluoride with the precursor N,N,N-trimethyl-5-((2,3,5,6-tetrafluorophenoxy)-carbonyl)pyridin-2-aminium trifluoromethanesulfonate:

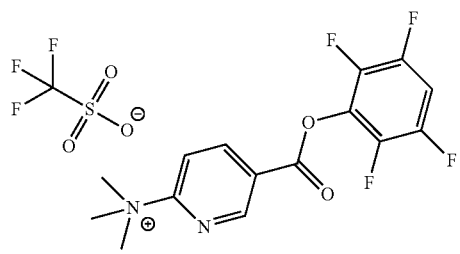 [SMILES: O=S(=O)([O-])C(F)(F)F ; C[N+](C)(C)c1ccc(C(=O)Oc2c(F)c(F)cc(F)c2F)cn1]

[$^{18}$F]F-Py-TFP and its synthesis from N,N,N-trimethyl-5-((2,3,5,6-tetrafluorophenoxy)-carbonyl)pyridin-2-aminium trifluoromethanesulfonate are described in WO 2010/114723 and in Olberg et al., Journal of Medicinal Chemistry, 53, 1732-1740 (2010), the contents of which are incorporated herein by reference.

[$^{18}$F]F-Py-TFP is an active ester and forms stable amide bonds with amine functionalities found in many biomolecules. Additionally, the [$^{18}$F]fluoropyridine moiety that is incorporated into the biomolecule has a low lipophilic impact on the biomolecule thus favouring renal excretion and low unspecific binding of the PET tracer.

The conventional synthesis of [$^{18}$F]F-Py-TFP, as described in WO 2010/114723 and Olberg et al., is based on the following steps:

Preparation of the Fluorinating Agent:

The radionuclide ($^{18}$F) is produced in advance by irradiation of $^{18}$O enriched water with a proton beam produced in a particle accelerator, giving $^{18}$F$^-$ or H$^{18}$F in an aqueous solution. The radionuclide-containing solution is then passed through a column containing a solid-phase support (typically an anion-exchange resin) which traps the [$^{18}$F] fluoride in the column.

The $^{18}$F anion is activated by eluting the trapped [$^{18}$F] fluoride from the anion-exchange resin into a reaction vessel. The elution is accomplished using a phase transfer catalyst (PTC) such as tetrabutylammonium bicarbonate (TBA-HCO$_3$). It is of major importance that the elution solution (i.e. the solution containing the phase transfer agent or agents) is alkaline to render the fluoride nucleophilic, and to minimize evaporation of H$^{18}$F gas in the following step.

2. Labelling of the Precursor:

The fluorinating agent (i.e. [$^{18}$F]fluoride) is made anhydrous by subsequent additions of acetonitrile (CH$_3$CN) to the reaction vessel and evaporation using heat (90 to 100° C.) and a sweep gas (N$_2$ or He). After cooling of the reaction vessel to 40° C., the precursor N,N,N-trimethyl-5-((2,3,5,6-tetrafluorophenoxy)-carbonyl)pyridin-2-aminium trifluoromethanesulfonate dissolved in 1 mL of a 1:1 mixture of acetonitrile and tert-butyl alcohol is then added to the dry TBA-$^{18}$F residue. An aromatic nucleophilic substitution reaction in which the N,N,N-trimethylaminium of the precursor is displaced by the $^{18}$F atom, results in the formation of [$^{18}$F]fluoronicotinic acid 2,3,5,6-tetrafluorophenyl ester ([$^{18}$F]F-Py-TFP). This reaction normally takes 10 minutes. The true incorporation yields of $^{18}$F are around 50-60%, due to decomposition of the precursor and sticking of fluoride to the reaction vessel, as described in Olberg et al.

This conventional procedure has, however, a number of drawbacks, including but not limited to the following:

- The overall duration of the process is at least 20 minutes, mainly due to the number of successive drying steps needed to render the $^{18}$F anhydrous and subsequent cooling of the reaction vessel prior to the addition of fluoride.
- Most commercial PET synthesizer platforms are only equipped with a single reaction vessel. This will be contaminated for the next synthesis step where [$^{18}$F]F-Py-TFP is reacted with the biomolecule in question. This makes it challenging to accommodate a full $^{18}$F-biomolecule preparation process using the above-described procedure on an automated commercial platform.
- The need for a phase-transfer-catalyst necessitates a limit test for its presence in the final drug product—a time-consuming quality control test that allows $^{18}$F to decay further before product release.
- The use of a weak base such as HCO$_3^-$ during elution makes the fluoride more prone to irreversible adsorption to the vessel wall making it unavailable for reaction with the precursor.

It is therefore desirable to provide an improved, e.g. a simpler and faster, process for the preparation of $^{18}$F-labelled compounds such as [$^{18}$F]F-Py-TFP which overcomes these drawbacks.

In recent years there has been increasing interest in so-called "on-column" or "solid phase" radiofluorination. In such methods the [$^{18}$F] fluoride is not eluted from the column for subsequent reaction with a precursor (prosthetic group) in a reaction vessel. Instead, the precursor and the [$^{18}$F]fluoride undergo reaction on the column itself, i.e. in-situ. However, "on-column" radiofluorination processes reported so far in the literature suffer from poor yield and also have other drawbacks such as requiring significant heating in order to activate the $^{18}$F anion sufficiently to attain a reaction rate suitable for PET radiopharmaceutical manufacture. Mathiessen et al. (Molecules 2013, 18, 10531-10547) have recently reported on-column $^{18}$F labelling of small molecules using custom-made resins. However, this work suffered from a tedious process taking about 35-45 minutes, poor yields, and the need for elevated column temperatures. On-column methods of $^{18}$F radiolabelling have therefore so far not found commercial use.

The invention provides an alternative process for on-column radiofluorination in order to provide $^{18}$F-labelled compounds for use as prosthetic groups in the radiolabelling of biomolecules. More specifically, it provides an improved on-column radiofluorination process, e.g. one which is simpler, faster, and/or higher-yielding than those conventionally known in the art.

As employed herein, the term [$^{18}$F]fluoride, equivalently [$^{18}$F]F$^-$, refers to a fluoride anion (F$^-$) in which the fluorine isotope is fluorine-18. Similarly, where compound names include the notation [$^{18}$F], for example in reference to an "[$^{18}$F]fluoro-" substituent, this indicates that the fluorine substituent in that compound is a fluorine-18 atom. Where more than one fluorine atom is present in a radiofluorinated molecule as herein described, the molecule should be understood as containing only one fluorine-18 substituent unless otherwise indicated, all other fluorine atoms in the molecule being of the $^{19}$F isotope (fluorine-19 is the only stable naturally-occurring isotope of fluorine: isotopes of fluorine other than $^{18}$F and $^{19}$F have half-lives of under a minute and therefore have negligible abundance). The [$^{18}$F] notation in such cases will appear adjacent to the fluorine-18 substituent. Thus, for example, in [$^{18}$F]fluoronicotinic acid 2,3,5,6-tetrafluorophenyl ester, the fluorine-18 atom is the fluorine substituent on the nicotinic acid moiety, with the four fluorine atoms in the tetrafluorophenyl moiety being fluorine-19 atoms. In the case of any ambiguity in nomenclature in polyfluorinated compounds, the position of the $^{18}$F isotope indicated in the corresponding structural formula should be regarded as definitive.

In a first aspect the present invention provides a radiofluorination process which comprises the following steps:
(a) providing a solid stationary phase which comprises a polymeric anion-exchange resin having bound thereto [$^{18}$F]fluoride anions; and
(b) contacting said solid stationary phase with a non-aqueous solution of a precursor compound of formula (I):

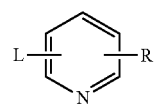

(I)

optionally in the presence of an organic non-nucleophilic base, whereby to produce a radiofluorinated compound of formula (II):

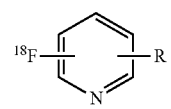

(II)

wherein:
in formula (I), L is a positively charged leaving group, e.g. a leaving group selected from —NH$_3^+$, —N(C$_{1-6}$ alkyl)$_3^+$, 1,4-diazabicyclo[2.2.2]octan-1-ium, and 1-(C$_{1-3}$ alkyl)-pyrrolidin-1-ium; and
in formulae (I) and (II), R is a group of the formula:

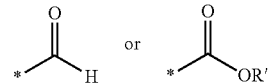

wherein R' is an electron-withdrawing group.

Although the use of an organic non-nucleophilic base in step (b) is optional, the presence of such a base is preferred. Therefore, in a preferred embodiment, in step (b) the solid stationary phase is contacted with the non-aqueous solution of the precursor compound of formula (I) in the presence of an organic non-nucleophilic base. Thus, in this embodiment, the present invention provides a radiofluorination process which comprises the following steps:

(c) providing a solid stationary phase which comprises a polymeric anion-exchange resin having bound thereto [$^{18}$F]fluoride anions; and (d) contacting said solid stationary phase with a non-aqueous solution of a precursor compound of formula (I):

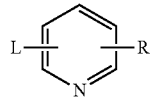

(I)

optionally in the presence of an organic non-nucleophilic base, whereby to produce a radiofluorinated compound of formula (II):

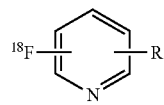

(II)

wherein:

in formula (I), L is a positively charged leaving group, e.g. a leaving group selected from —NH$_3^+$, —N(C$_{1-6}$ alkyl)$_3^+$, 1,4-diazabicyclo[2.2.2]octan-1-ium, and 1-(C$_{1-3}$ alkyl)-pyrrolidin-1-ium; and in formulae (I) and (II), R is a group of the formula:

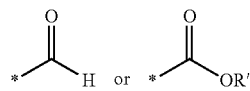

wherein R' is an electron-withdrawing group.

The symbol * indicates the point of attachment of group R to the pyridinyl ring.

The precursor compound of formula (I) is optionally in the form of a salt, e.g. a salt with a suitable counterion such as a chloride, bromide, phosphate, metaphosphate, perchlorate, nitrate, sulphate, tartrate, trifluoroacetate, citrate, malate, lactate, fumarate, benzoate, glycolate, gluconate, succinate, methanesulphonate, trifluoromethanesulphonate, or para-toluenesulphonate anion.

In the precursor compound of formula (I), groups L and R may be located in ortho-, meta- or para-positions relative to one another on the pyridinyl ring. Groups L and R may independently be located in the ortho-, meta- or para-position relative to the nitrogen atom of the pyridinyl ring, i.e. these may be located at any of the available ring positions.

The precursor compound of formula (I) may be selected from a compound of formula (Ia), (Ib), (Ic) or (Id):

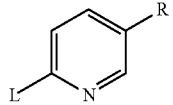

(Ia)

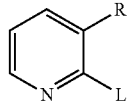

(Ib)

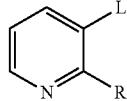

(Ic)

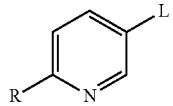

(Id)

(wherein L and R are as herein defined)
or a salt thereof with a suitable counterion, e.g. one as herein defined.

Precursor compounds of formulae (Ia) and (Ib) are preferred. In an embodiment the compound of formula (I) is a compound of formula (Ia) in which L and R are para-relative to one another.

As noted above, L is a positively charged leaving group and may, for example, be a leaving group selected from —NH$_3^+$, —N(C$_{1-6}$ alkyl)$_3^+$, 1,4-diazabicyclo[2.2.2]octan-1-ium, and 1-(C$_{1-3}$ alkyl)-pyrrolidin-1-ium. All leaving groups L are thus positively charged. Without wishing to be bound by theory, the present inventors believe that the positive charge assists in the release of [$^{18}$F]fluoride anions from the stationary phase. This provides the advantage that the process of the invention can be performed without the need to employ a phase transfer catalyst. The presence of a positively-charged leaving group also increases the electron deficiency of the pyridine ring (which is already slightly electron deficient compared to a homoaromatic system such as a phenyl ring), increasing the reactivity of the precursor towards aromatic nucleophilic substitution by the released [$^{18}$F]fluoride anions. This reactivity is still further enhanced by the presence of group R, which contains at least an electron-withdrawing carbonyl group as well as (in certain embodiments) a further electron-withdrawing group R'. Homoaromatic analogues of the precursor compounds of formula (I) do not display the same reactivity and therefore the high reactivity, fast reaction time and good yields achieved by the process of the invention were not expected prior to carrying out the work described herein.

A preferred leaving group L of the type —N(C$_{1-6}$ alkyl)$_3^+$ is —N(CH$_3$)$_3^+$ (i.e. a trimethylammonium group). A preferred leaving group L of the type 1-(C$_{1-3}$ alkyl)-pyrrolidin-1-ium is 1-methylpyrrolidin-1-ium.

In an embodiment the leaving group L is —N(CH$_3$)$_3^+$ (trimethylammonium), 1-methylpyrrolidin-1-ium, or 1,4-diazabicyclo[2.2.2]octan-1-ium. The abbreviation "DABCO" may be employed to refer to a 1,4-diazabicyclo[2.2.2]octan-1-ium leaving group.

The leaving group L is positively charged and therefore a suitable counterion (i.e. an anion) will normally be present as part of the precursor compound of formula (I). Any suitable counterion may be employed with any leaving group L. Suitable counterions for any leaving group L herein described include those described above, i.e. chloride, bromide, phosphate, metaphosphate, perchlorate, nitrate, sulphate, tartrate, trifluoroacetate, citrate, malate, lactate, fumarate, benzoate, glycolate, gluconate, succinate, methanesulphonate, trifluoromethanesulphonate, and para-toluenesulphonate anions. In an embodiment the counterion is a chloride, bromide, perchlorate, sulphonate, nitrate, phosphate, or trifluoromethanesulphonate anion. Perchlorate or trifluoromethanesulphonate anions are preferred. The trifluoromethanesulphonate anion may be referred to as triflate, -OTf, OTf⁻ or simply OTf.

In certain embodiments, the group R in the precursor compounds of formula (I) is an aldehyde group, —CHO. This gives rise to the possibility of the following precursor compounds of formula (Ie), (If), (Ig) and (Ih) and their salts:

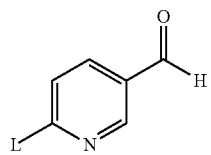
(Ie)

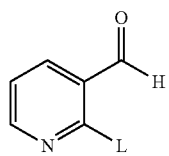
(If)

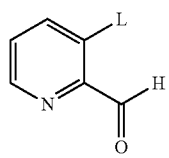
(Ig)

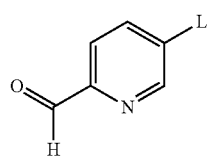
(Ih)

In these compounds the leaving group L is as hereinbefore defined.

Precursor compounds of formulae (Ie) and (If) are preferred. In an embodiment the compound of formula (I) is a compound of formula (Ie), in which L and the aldehyde group are para-relative to one another.

In certain embodiments, the group R in precursor compounds of formula (I) is —COOR', wherein R' is an electron-withdrawing group. This gives rise to the possibility of the following precursor compounds of formula (Ii), (Ij), (Ik) and (Il) and their salts:

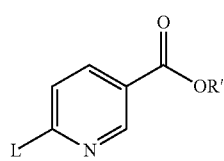
(Ii)

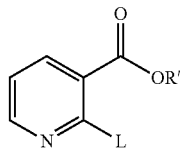
(Ij)

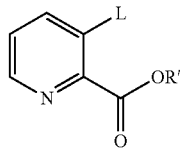
(Ik)

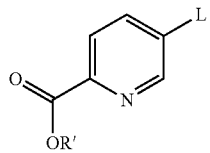
(Il)

In these compounds the leaving group L is as hereinbefore defined.

Precursor compounds of formulae (Ii) and (Ij) are preferred. In an embodiment the compound of formula (I) is a compound of formula (Ii) in which the L and the ester group are para-relative to one another.

Where R is —COOR' (thus in precursor compounds of formulae (Ii), (Ij), (Ik) and (Il)) the precursor compound may be described as an "active ester" (or "activated ester") because the carbonyl group of the —COOR' substituent is electron-deficient and the —OR' moiety of the —COOR' substituent is a good leaving group. The corresponding radiofluorinated compounds of formula (II) derived from such precursor groups may also be described as "active esters" (or "activated esters") for the same reasons. Due to the electron-deficiency of the carbonyl group and the ability of the —OR' group to act as a leaving group, "active esters" are "activated" to form amide bonds via condensation reactions with amine groups such as amine side-chains in biomolecules (e.g. peptides). Although other compounds are also capable of amide bond formation, active esters are particularly advantageous due to their increased reactivity and capability to react under mild aqeuous reaction conditions. Radiofluorinated active esters are therefore particularly good radiolabelling agents for the radiolabelling of biomolecules. Methods for on-column $^{18}$F-labelling of "activated esters" to generate $^{18}$F-labelled compounds suitable for use as prosthetic groups were unknown prior to the present invention.

The electron withdrawing group R' may be any substituent which has a tendency to withdraw electron density from the carbonyl carbon atom (i.e. which is more electronegative than the carbonyl group) and which thus increases the susceptibility of the carbonyl group to nucleophilic attack. In an embodiment the electron withdrawing group R' is —CX$_3$ or —CH$_2$CX$_3$ (where each X is independently Cl or F), —CH(CX$_3$)$_2$ or —C(CX$_3$)$_3$ (where each X is independently Cl or F, and each CX$_3$ group may be the same or different), or a group having the structure -Ph(Z)$_n$:

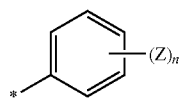

(where n is an integer from 1 to 5 (i.e. 1, 2, 3, 4 or 5, preferably 1 or 4) and each Z is independently an electron withdrawing group, e.g. —F, —NO$_2$, or —CN).

In the above structural formula for the group -Ph(Z)$_n$, the symbol * indicates the point of attachment of the phenyl ring to the non-carbonyl oxygen atom of the ester group, such that where R' is a -Ph(Z)$_n$ group, then group R has the structure:

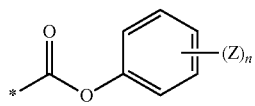

(where * indicates the point of attachment of the group R to the pyridyl ring of the compound of formula (I)).

In an embodiment the electron withdrawing group R' is —CF$_3$, —CH$_2$CF$_3$, —CH(CF$_3$)$_2$, —C(CF$_3$)$_3$, or -Ph(Z$_n$.

The precursor compound of formula (I) may be a compound of formula (Im) or (In):

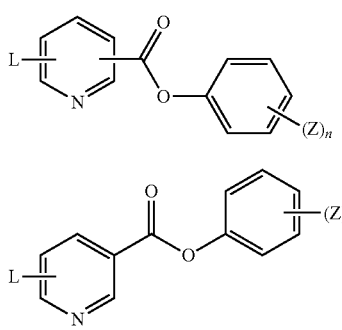

wherein L, Z and n are as herein defined.

Where the electron withdrawing group R' is a -Ph(Z)$_n$, group, n may be 1, 2, 3, 4 or 5 in formula (Im) or (In). Where n is 1, 2, 3, or 4, multiple regioisomers of group -Ph(Z)$_n$ exist which vary in their placement of groups Z around the ring. All such regioisomers are contemplated within the scope of the compounds of formula (I) as defined herein. Thus, where n=1, group R' may have any one of the following structures:

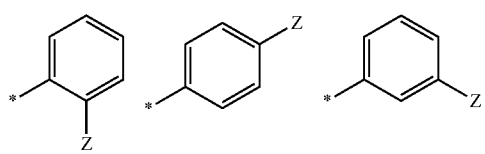

Where n=2, group R' may have any one of the following structures:

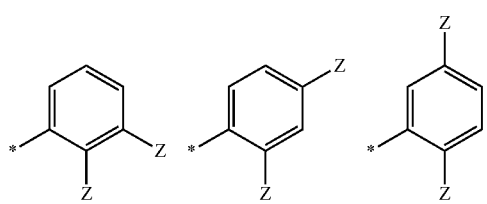

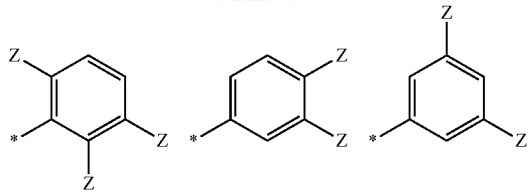

Where n=3, group R' may have any one of the following structures:

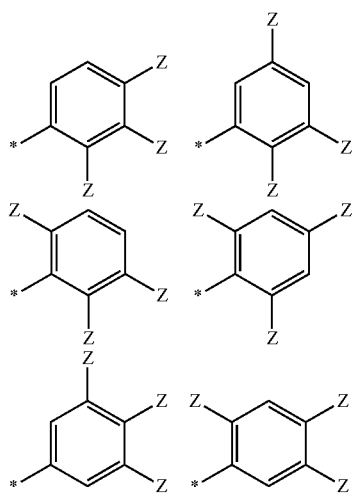

Where n=4, group R' may have any one of the following structures:

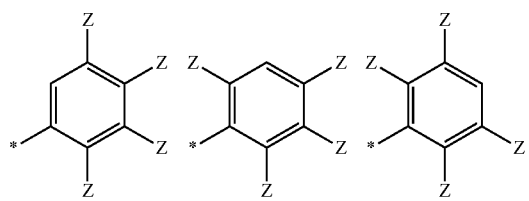

Where n=5, group R' has the following structure:

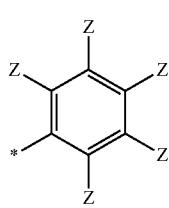

In all of the above structures each group Z, independently of one another, may be as herein defined. As will be appreciated, in embodiments where n is 2, 3, 4 or 5, multiple further regioisomers may also exist where the individual groups Z are not identical to one another. All such regioisomers are contemplated within the scope of the compounds of formula (I) as described herein.

Examples of electron withdrawing groups R' having formula -Ph(Z)$_n$ include, but are not limited to, -Ph(NO$_2$), -Ph(CN), -PhCl, -PhCl$_2$, -PhCl$_3$, -PhCl$_4$, -PhCl$_5$, -PhF, -PhF$_2$, -PhF$_3$, -PhF$_4$, -PhF$_5$, -PhClF, -PhClF$_2$, -PhClF$_3$, -PhClF$_4$, -PhFCl$_2$, -PhFCl$_3$, -PhFCl$_4$, and -PhF$_2$Cl$_2$ (all regioisomers of such groups are contemplated where such regioisomers can exist).

In preferred embodiments the precursor compound of formula (I) may be a compound of formula (Io), (Ip), (Iq) or (Ir), or a salt thereof:

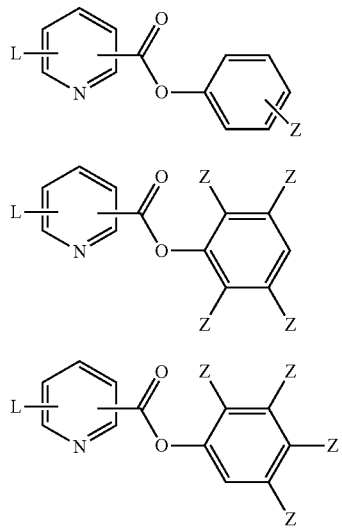

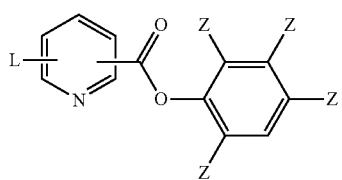

In all compounds of formulas (Ia) to (Ir), L is a leaving group as hereinbefore defined and is preferably —N(CH$_3$)$_3$$^+$ (trimethylammonium), 1-methylpyrrolidin-1-ium, or 1,4-diazabicyclo[2.2.2]octan-1-ium.

Preferred precursor compounds for use in the invention are those of formula (Is) and their salts:

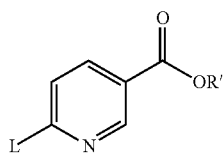

wherein L and R' are as defined in Table 1:

TABLE 1

| L | R' | | | | | | |
|---|---|---|---|---|---|---|---|
| | F-C6F4-CH2- (pentafluorophenyl-CH2) | 4-NO2-C6H4-CH2- | (CF3)2CH- | (CF3)3C- | 3,4,5-F3-C6H2-CH2- | 2,4-Cl2-C6H3-CH2- | 2,3,5-F3-4-Cl-C6H-CH2- |
| -N+(CH3)3 | (1) | (2) | (3) | (4) | (5) | (6) | (7) |
| N-methylpyrrolidinium | (8) | (9) | (10) | (11) | (12) | (13) | (14) |
| DABCO+ | (15) | (16) | (17) | (18) | (19) | (20) | (21) |

This gives rise to compounds (1) to (21) and their corresponding salts.

In a particularly preferred embodiment the precursor compound of formula (I) is selected from compounds (1), (8) and (15) as defined in Table 1 (and their salts). Compound (1) is especially preferred. Compound (1) is N,N,N-trimethyl-5-((2,3,5,6-tetrafluorophenoxy)-carbonyl)pyridin-2-aminium trifluoromethanesulfonate.

In the process of the invention the precursor compound of formula (I) reacts with the [¹⁸F]fluoride anions eluted from the solid stationary phase by undergoing nucleophilic aromatic substitution. This results in leaving group L being replaced by an [¹⁸F]fluoro-substituent (also denoted as an [¹⁸F]F substituent) to produce a radiofluorinated compound of formula (II):

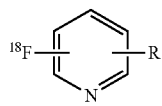

(II)

In the radiofluorinated compound of formula (II), the [¹⁸F]F substituent occupies the same position on the pyridyl ring previously occupied by the leaving group L. The group R remains unchanged. Therefore, all preceding discussion of groups R, R' and Z in the context of precursor compounds of formula (I) applies equally to the radiofluorinated prosthetic group of formula (II). Consequently, the radiofluorinated compound of formula (II) may be a compound of formula (IIa), (IIb), (IIc), (IId), (IIe), (IIf), (IIg), (IIh), (IIi), (IIj), (IIk), (IIl), (IIm), (IIn), (IIo), (IIp), (IIq), (IIr) or (IIs). Such compounds have structures analogous to compounds of formulae (Ia), (Ib), (Ic), (Id), (Ie), (If), (Ig), (Ih), (Ii), (Ij), (Ik), (Il), (Im), (In), (Io), (Ip), (Iq), (Ir) or (Is), respectively, but with an [¹⁸F]F atom in place of the leaving group L.

Where the compound of formula (I) is selected from compounds (1) to (21) as defined in Table 1, the corresponding radiolabelled prosthetic groups formed by reaction with the [¹⁸F]fluoride anion have general formula (IIs):

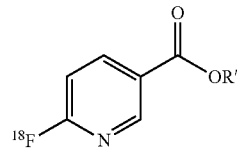

(IIs)

wherein:

precursor compounds (1), (8) and (15) each react with the [¹⁸F]fluoride anion to form a radiolabelled prosthetic compound (1'); precursor compounds (2), (9) and (16) each react with the [¹⁸F]fluoride anion to form a radiolabelled prosthetic compound (2'); precursor compounds (3), (10) and (17) each react with the [¹⁸F]fluoride anion to form a radiolabelled prosthetic compound (3'); precursor compounds (4), (11) and (18) each react with the [¹⁸F]fluoride anion to form a radiolabelled prosthetic compound (4'); precursor compounds (5), (12) and (19) each react with the [¹⁸F]fluoride anion to form a radiolabelled prosthetic compound (5'); precursor compounds (6), (13) and (20) each react with the [⁸F]fluoride anion to form a radiolabelled prosthetic compound (6'); and precursor compounds (7), (14) and (21) each react with the [¹⁸F]fluoride anion to form a radiolabelled prosthetic compound (7'); and wherein the R' group in general formula (IIs) in respect of each of radiolabelled prosthetic compounds (1') to (7') is as defined in Table 2:

TABLE 2

| R' | | | | |
|---|---|---|---|---|
| Prosthetic compound | (1') | (2') | (3') | (4') |
| R' | | | | |
| Prosthetic compound | (5') | (6') | (7') | |

Where the compound of formula (I) is compound (1), (8) or (15) as defined in Table 1, the resulting radiofluorinated prosthetic compound of formula (II) is [¹⁸F]fluoronicotinic acid 2,3,5,6-tetrafluorophenyl ester ([¹⁸F]F-Py-TFP) which is a compound of formula (1') as defined in Table 2. This is a particularly preferred radiofluorinated prosthetic group.

In the process according to the invention, the precursor compound of formula (I) is provided in a non-aqueous solution. The non-aqueous solution may be referred to as the "precursor solution". The precursor solution comprises the precursor compound of formula (I) and a non-aqueous solvent.

Any suitable organic solvent may be employed as the non-aqueous solvent, such as acetonitrile ("ACN"), tert-butanol, dimethylformamide ("DMF"), dimethylsulphoxide ("DMSO"), dimethylacetamide, tetrahydrofuran, dioxan, 1,2-dimethoxyethane, sulpholane, N-methylpyrolidinone, or mixtures thereof. Alternatively an ionic liquid may be employed as the non-aqueous solvent, such as an imidazolium derivative (e.g. 1-ethyl-3-methylimidazolium hexafluorophosphate), a pyridinium derivative (e.g. 1-butyl-4-methylpyridinium tetrafluoroborate), a phosphonium compound, a tetraalkylammonium compound, or mixtures thereof. The preferred non-aqueous solvent is a mixture of acetonitrile and tert-butanol in a ratio of from 1:1 to 1:9 such as 1:1 to 2:8, preferably 1:1 or 2:8.

The volume of the precursor solution to be used in the method can readily be determined by those skilled in the art and will be dependent on factors such as the nature of the column employed. Typically, this may have a volume of 1-5000 μL, preferably 300-1500 μL.

In the process of the invention the precursor compound of formula (I) is optionally contacted with the stationary phase in the presence of an organic non-nucleophilic base. The presence of an organic non-nucleophilic base is preferred as this can be beneficial. Suitable organic non-nucleophilic bases include N,N-diisopropylethylamine (DIPEA or Hünig's base), trimethylamine (TEA), and sym-collidine (and its isomers). In an embodiment the precursor solution comprises 1 to 3 stoichiometric equivalents (eq.) of the organic non-nucleophilic base with respect to the precursor compound. In a preferred embodiment the base is DIPEA or trimethylamine. Trimethylamine is particularly preferred as this is less expensive and excess trimethylamine can be removed more easily. In a particularly preferred embodiment of the invention DIPEA or trimethylamine is employed in an amount of about 10 to about 15 μl together with about 20 to about 40 (e.g. about 30) mg of precursor compound. This embodiment has been found to give particularly advantageous overall yields (about 60 to about 70%) of the corresponding radiolabelled prosthetic group. This embodiment has also been found to give particularly reproducible results.

In an alternative embodiment the stationary phase is pre-loaded (pre-charged) with the organic non-nucleophilic base prior to introduction of the precursor solution. The term "stationary phase" is a common term of the art in the field of chromatography and refers to one of the two phases of a chromatographic system, the other phase being referred to as the mobile phase. The mobile phase flows through or over the stationary phase. In the process of the present invention the precursor solution acts as the mobile phase.

According to the invention, the solid stationary phase comprises a polymeric anion-exchange resin. The solid stationary phase may consist essentially of the polymeric anion-exchange resin or the polymeric anion-exchange resin may be supported on an inert solid support material. The anion exchange resin and/or the inert solid support material (where present) may be in the form of a resin, grains, beads, membranes, sheets and/or capillaries. The anion-exchange resin is a polymeric anion-exchange resin, preferably an organic polymeric anion-exchange resin and not a silica-based anion-exchange resin, since silica-based anion-exchange resins (particularly silica-based, hydrophilic, strong ion exchanger materials) have been found to work less efficiently with the process of the invention.

The polymeric anion-exchange resin is preferably a strong anion-exchange resin but may also be a weak anion exchange resin or a mixture of strong and weak anion-exchange resins. The polymeric anion-exchange resin may for example be a resin derived from a polystyrene-divinyl-benzene copolymer or derived from a so-called "Merrifield resin" which is a copolymer of styrene and chloromethylstyrene. Preferred counter-ions for the anion exchange resin are bicarbonate ($HCO_3^-$), dihydrogen phosphate, monohydrogen phosphate, or any other inorganic or organic anion with a $pK_a$ value of 7 to 12. Where the precursor compound of group (I) is an active ester, the counter-ion for the anion exchange resin is preferably only weakly basic in order to avoid base hydrolysis of the R group of the precursor compound. In such cases bicarbonate is particularly preferred as the counter-ion for the anion exchange resin.

The polymeric anion-exchange resin may be provided in a chromatographic column or cartridge. The term "column" or "cartridge" means any type of conventional stationary phase apparatus which may be used in chromatography, including plastic or glass containers which contain the anion-exchange resin and allow a mobile phase to be introduced at a first end from where it flows through or over the stationary phase under gravity and/or pressure to a second end.

Suitable anion exchange materials and chromatographic columns or cartridges bearing such anion exchange materials are commercially available and known to those skilled in the art. Examples of suitable commercially-available polymeric anion-exchange materials and columns/cartridges bearing anion-exchange materials include those available under the following trade names:

From Macherey-Nagel:
CHROMABOND strong PS/DVB-anion exchanger in $HCO_3$-form (PS—$HCO^-_3$) shorty/45 mg
CHROMABOND strong PS/DVB-anion exchanger in other ionic forms, shorty/45 mg From Waters:
Oasis MAX Plus Short Cartridge, 225 mg Sorbent per Cartridge, 60 μm Particle Size
Oasis WAX Plus Short Cartridge, 225 mg Sorbent per Cartridge, 60 μm Particle Size From Thermo Scientific:
HyperSep™ SAX Cartridges From Bio-Rad:
AG resins with quaternary ammonium functional groups From GL sciences:
MonoSpin™ SAX From PerkinElmer:
SPE Supra-Clean® Strong Anion Exchange (SAX)

From Supelco:
Supel-Select SAX

From Phenomenex:
Strata-X-A and products with similar characteristics

From Silicycle:
SiliaPrepX™ SAX Polymeric SPE Cartridges

From Avantor:
Bakerbond Xwp 500 Polyquat-35

The columns/cartridges available from Macherey-Nagel GmbH & Co. KG, Düren, Germany, under the trade names Chromafix® and Chromabond® are particulary preferred in the processes of the invention, in particular the Chromafix® and Chromabond® PS—$HCO_3$® and PS—$CO_3^-$ anion exchange columns.

The required amount of solid phase can readily be determined by those skilled in the art and will be dependent on factors such as the nature of the column employed. Typically, the solid phase may be provided in an amount of 1 mg to 1000 mg, preferably 5 mg to 130 mg.

When the precursor solution contacts the stationary phase it elutes [$^{18}$F]fluoride anions from the stationary phase and thus "activates" the anions for nucleophilic substitution of the leaving group L. It is therefore necessary to trap [$^{18}$F] fluoride anions on the polymeric anion-exchange resin before contacting the stationary phase with the precursor solution.

The preparation and trapping of [$^{18}$F] may be performed using conventional methods. [$^{18}$F]fluoride may conveniently be prepared from $^{18}$O-enriched water using the (p,n) nuclear reaction as described by Guillaume et al. (Appl. Radiat. Isot. 42 (1991) 749-762). [$^{18}$F]fluoride is generally isolated as an aqueous solution of H[$^{18}$F]F or a salt such as Na[$^{18}$F]F, K[$^{18}$F]F, Cs[$^{18}$F]F, a tetraalkylammonium[$^{18}$F]fluoride (e.g. tetramethylammonium[$^{18}$F]fluoride) or tetraalkylphosphonium[$^{18}$F]fluoride (e.g. tetramethylphosphonium[$^{18}$F]fluoride).

The [$^{18}$F]fluoride can be trapped on the stationary phase by passing the [$^{18}$F]fluoride-containing aqueous solution (typically in an amount of 1 to 5 ml) over or through the stationary phase, which traps the [$^{18}$F]fluoride in the anion-exchange resin.

Prior to trapping the [$^{18}$F]fluoride on the statoinary phase, it may be preferable to "condition" the resin with bicarbonate (HCO$_3^-$) counter-ions. This may be performed according to conventional methods known to those skilled in the art.

In order to remove any bulk water remaining in the stationary phase following the trapping of the [$^{18}$F]fluoride, the stationary phase is preferably rinsed with an organic water-miscible solvent such as acetonitrile before contacting the [$^{18}$F]fluoride-bearing stationary phase with the precursor solution. The organic solvent will also function as a conditioning medium for the stationary phase. Preferably 0.05 to 10 ml of organic water-miscible solvent, e.g. about 2 mL, are used for rinsing the stationary phase.

Optionally the stationary phase may be further dried with air, argon, N$_2$ or other inert gas after rinsing with the organic water-miscible solvent and before the elution step. For example, the stationary phase may be dried with 5-10 ml of air, argon, N$_2$ or other inert gas after rinsing with the organic water-miscible solvent and before the elution step.

The step of eluting the trapped [$^{18}$F]fluoride anions from the stationary phase is effected by contacting the stationary phase with the precursor solution. Preferably, this is carried out by eluting the precursor solution through the stationary phase at a rate of <1.0 mL/minute. Preferably the elution is performed for about 1 to 3 minutes, e.g. for about 2 to 3 minutes.

Surprisingly, the use of an electron-deficient precursor compound of formula (I) together with a polymeric anion-exchange material allows direct on-column reaction between the precursor and the [$^{18}$F]fluoride without the need for a phase transfer catalyst. Thus in an embodiment of the invention the method is not carried out in the presence of a phase transfer catalyst (such as those phase transfer catalysts commonly used in PET radiochemistry for nucleophilic reactions with [$^{18}$F]fluoride), for example the stationary phase is not contacted with a phase transfer catalyst during the elution step.

Following preparation of the compound of formula (II), the stationary phase may if desired be rinsed with an organic solvent and/or an acidic aqueous solution (or a mixture of an organic solvent and an acidic aqueous solution) in order to recover any residual compound of formula (II) which may have remained on the stationary phase after the precursor solution has passed through or over the stationary phase. Any organic solvent as herein described is suitable for this purpose.

Previously-described attempts at on-column fluorination described in the literature require heating of the anion-exchange resin and/or precursor solution to elevated temperatures of 40° C. or more, such as 70-90° C. Such temperatures are not accessible on commercial radiofluorination platforms such as those used in hospitals or other clinical settings. In contrast, the process of the invention can be carried out at ambient temperature. In an embodiment the process of the invention is performed at a temperature of 35° C. or below, preferably 30° C. or below, e.g. a temperature of from 10° C. to 25° C., such as 15° C. to 25° C., 18° C. to 23° C. or 20 to 25° C.

As the process of the invention does not require the use of a phase transfer catalyst, it is much simpler than radiofluorination processes known in the art. In part, this is because it is not necessary to purify the compound of formula (II) in order to remove residual phase transfer catalyst, or to perform quality control for the presence of phase transfer catalyst in the final radiolabelled product. However, following the preparation of the compound of formula (II) it may nevertheless, if desired, be purified by standard methods, typically using solid phase extraction, for example with an Oasis MCX™ column or a SEP-PAK™ C18 plus column from which the compound of formula (II) can be eluted with good purity using a suitable organic solvent/water mixture. Such purification may be performed in order to remove intact precursor, unreacted $^{18}$F$^-$ and other non-radioactive impurities deriving from the precursor.

The lack of a requirement for a phase transfer catalyst means that no separate eluent solution containing a phase transfer agent is required to elute the [$^{18}$F]fluoride from the stationary phase to a reaction vessel before reaction with the precursor compound can take place. Only one vial is needed, which can contain the precursor compound, a base (where this is present) and a non-aqueous solvent. This saves space, capacity and materials. Alternatively, the precursor can be stored separately from the base and mixed with the base and solvent at the point of use, e.g. just before synthesis of the compound of formula (II); however, this still avoids the need for a separate phase transfer agent solution.

The radiolabelled product forms directly on the stationary phase (e.g. on the column) during the passage of the precursor solution through the stationary phase, and so a separate reaction vessel (separate from the stationary phase, e.g. the column or cartridge) for preparation of the compound of formula (II) is not needed.

The reaction between the precursor compound of formula (I) and the [$^{18}$F]fluoride anions in the process of the invention is rapid and is essentially complete within 5 minutes (often as little as 2 to 3 minutes) with no requirement for heating or cooling.

Commercially available PET automatic synthesizer platforms are normally equipped with one reaction vessel. The present invention therefore avoids the need to use the reaction vessel for incorporation of [$^{18}$F]F into the precursor. The reaction vessel will therefore be un-used and clean (e.g. not contaminated with any radioactive residue) when it is used in a subsequent conjugation step between the compound of formula (II) and the selected biomolecule.

No azeotropic drying of the fluoride is required in the process of the present invention, unlike conventional methods. This results in improved yields due to less radioactive decay because of the shorter time needed to perform all process steps. The lack of azeotropic drying also avoids absorbance of $^{18}$F to the reaction vessel, unlike the conventionally-used azeotropic drying regime used in $^{18}$F PET chemistry. The lack of azeotropic drying also avoids producing volatile radioactive species.

The compounds of formula (II) can be used as prosthetic groups for the labelling of biomolecules. The compounds of formula (II) will conjugate to a biomolecule under mild conditions, for example via an [¹⁸F]fluoroacylation or [¹⁸F] fluoroamidation reaction with an amino group in a peptide such as an N^α-terminal amino group or a lysine N^ε-amino group of a peptide backbone.

In an embodiment the radiofluorination process of the present invention therefore further comprises the step of reacting the resulting compound of formula (II) with a compound of formula (III):

H₂N-biomolecule    (III)

to provide a radiolabelled biomolecule of formula (IV):

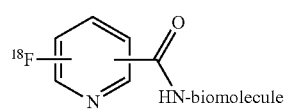

(IV)

(wherein in formulae (III) and (IV) "biomolecule" denotes a biomolecule or a residue or fragment thereof).

The reaction of a compound of formula (II) with a compound of formula (III) may be effected in a suitable solvent, depending on the biomolecule(III) solubility and stability in the said solvent, for example in an aqueous buffer in the pH range 2 to 12, suitably 7 to 11, and/or at a temperature in the range 5 to 70° C., preferably a temperature of 35° C. or below, preferably 30° C. or below, e.g. a temperature of 10° C. to 25° C., such as 15° C. to 25° C., 18° C. to 23° C. or 20 to 25° C. The choice of solvent, pH and temperature may depend on the solubility and stability of the biomolecule in the respective solvent under the selected conditions. The skilled person will readily be able to select an appropriate solvent, pH and temperature using their knowledge of the characteristics of the chosen biomolecule.

In formulae (III) and (IV) suitable biomolecules for labelling may readily be determined by those skilled in the art. These include peptides, for example somatostatin analogues (such as octreotide), bombesin, vasoactive intestinal peptide, chemotactic peptide analogues, α-melanocyte stimulating hormone, urea based PSMA inhibitors, neurotensin, Arg-Gly-Asp peptide and its analogues, human proinsulin connecting peptide, endothelin, angiotensin and formyl-norleucyl-leucyl-phenylalanyl-norleucyl-tyrosyl-lysine, or a residue or fragment thereof. Preferred peptides for labelling are Arg-Gly-Asp peptide ("RGD peptide") and its analogues, such as those described in WO 01/77415 and WO 03/006491, the entire contents of which are incorporated herein by reference.

In one embodiment, suitable peptides for use in the invention comprise the fragment:

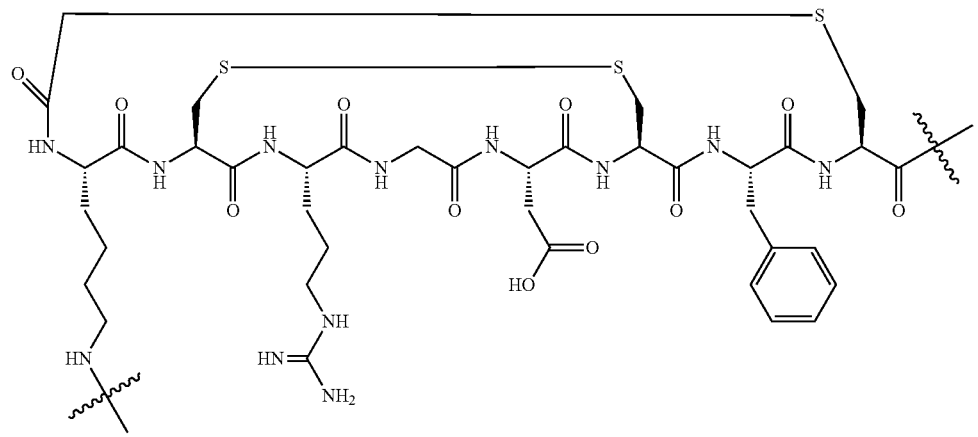 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

In one embodiment, the biomolecule in formula (III) or (IV) is a peptide having the following structure:

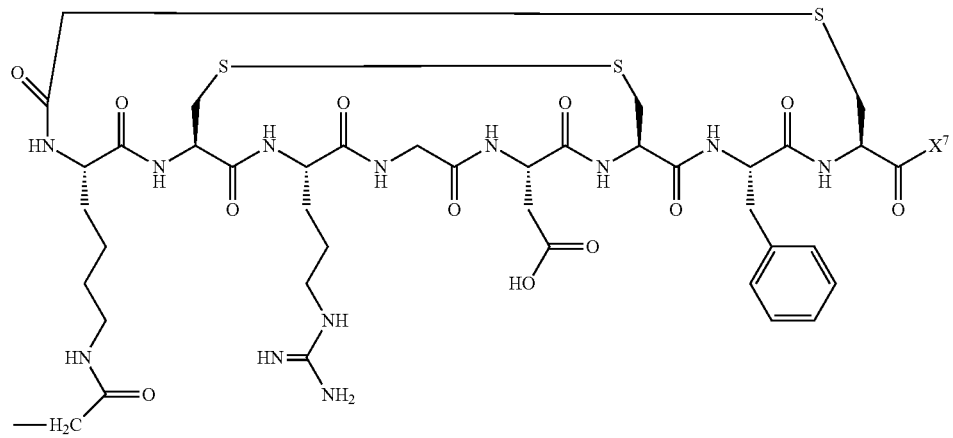

wherein X⁷ is either —NH₂ or a group of formula:

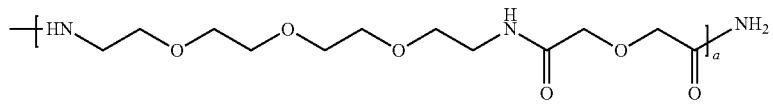

wherein a is an integer of from 1 to 10, preferably wherein a is 1.

In further embodiments the biomolecule in formula (III) or (IV) is a peptide having the following structure (C):

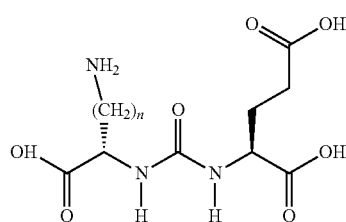

(C)

where n may be 1, 2, 3, 4, 5, 6, 7, 8 or 9.

The radiolabelled biomolecule of formula (IV) may therefore be a molecule of the following structure:

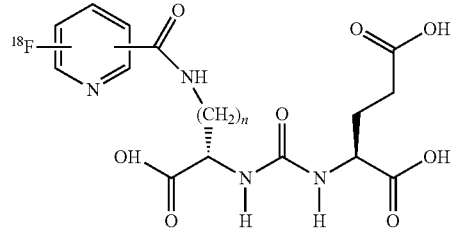

where n is 1, 2, 3, 4, 5, 6, 7, 8 or 9.

In another embodiment (corresponding to the peptide illustrated above where n=4) the biomolecule in formula (III) or (IV) is a peptide having the following structure:

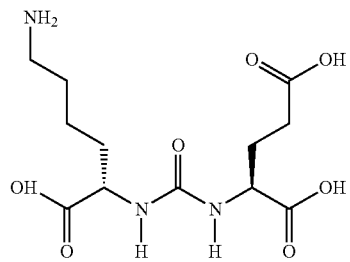 [SMILES: NCCCC[C@H](NC(=O)N[C@@H](CCC(=O)O)C(=O)O)C(=O)O]

The radiolabelled biomolecule of formula (IV) may therefore be a molecule of the following structure:

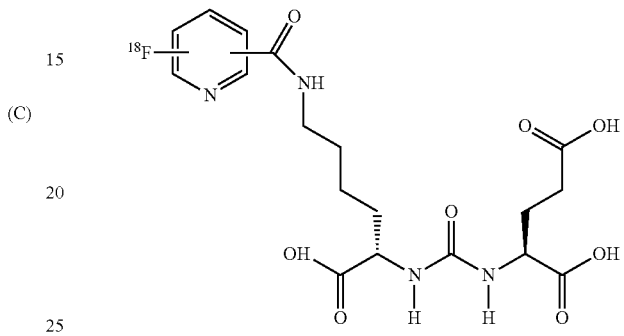

such as [$^{18}$F]DCFPyL (as described in Szabo et al., *Molecular Imaging and Biology*, 2015, vol. 17, issue 4, pp. 565-574):

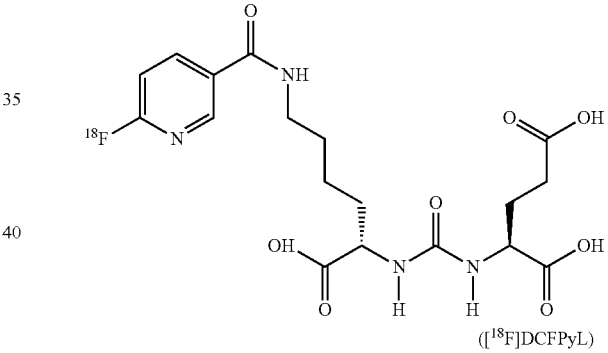

([$^{18}$F]DCFPyL)

[$^{18}$F]DCFPyL thus corresponds to the case where n=4, as noted above. Analogous radiolabelled biomolecules where n=1, 2, 3, 5, 6, 7, 8 or 9 may also be prepared and these also form part of the invention. Thus in one embodiment the invention provides a radiolabelled biomolecule of formula (D):

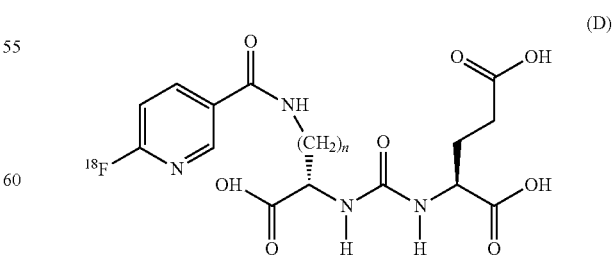

(D)

wherein n=1, 2, 3, 4, 5, 6, 7, 8 or 9.

Peptides of formula (C) bind to PSMA. Without wishing to be bound by theory, it is believed that varying the value of n allows the affinity to be varied so as to enhance or decrease the affinity of the peptide for PSMA. The radiolabelled biomolecules derived from such peptides may therefore also be tuned in their affinity for PSMA by appropriate selection of n. Radiolabelled biomolecules with lower values of n (particularly where n is 1, 2 or 3) are also excreted faster than those with higher values of n (i.e. where n is 4 or greater). This allows radioimaging to be performed at an earlier time point and with lower background.

In another embodiment, the biomolecule in formula (III) or (IV) is an aminooxy- or hydrazine-modified peptide, i.e. a peptide bearing an aminooxy or hydrazine group (e.g. as a side chain). Such modified peptides are well known to those skilled in the art and may be prepared by methods such as site-specific chemical protein conjugation using genetically encoded aldehyde tags as described by Rabuka et al., *Nature Protocols* 7, 1052-1067, 2012. Aminooxy and hydrazine groups react rapidly with aromatic aldehydes, forming oxime or hydrazone ligations, respectively. Thus aminooxy- or hydrazine-modified peptides are particularly advantageous peptides for reaction with radiofluorinated compounds of formula (II) wherein R is a group

(e.g. radiofluorinated compounds of formula (IIe), (IIf), (IIg) or (IIh) as herein defined), because this allows rapid conjugation. The reaction between a radiofluorinated compound of formula (II) wherein R is a group

is preferably performed at a pH of from about 2 to about 5, (e.g. pH 2-5, pH 2-4, pH 2-3, pH 3-5, or pH 4-5, such as pH 2, pH 3, pH 4 or pH 5) as this minimises reaction with free amine groups, which are protonated in this pH range, thereby allowing site-specific radiolabelling of the aminooxy and/or hydrazine groups of the modified peptide.

Aminooxy-modified peptides may have the following structure:

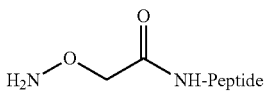

(wherein "peptide" denotes a peptide or a peptide residue or fragment).

An example of an aminooxy-modified peptide is Aminooxyacetyl-Leu-Glu-Phe-$NH_2$ as reported in, for example, Poethko et al., *The Journal of Nuclear Medicine*, Vol. 45, no. 5, May 2004.

An example of a hydrazine-modified peptide is 6-hydrazinopyridyl-functionalized human serum albumin (HYNIC-HSA) as reported in, for example, Dirksen et al., *Bioconjug. Chem.*, 2008, 19(12), 2543-2548.

As will be appreciated by the skilled person, the methods of the invention may also be used for [$^{18}$F]fluorination of other biomolecules, such as proteins, hormones, oligonucleotides, and antibody fragments, as well as small drug-like molecules to provide a variety of PET tracers.

Compounds of formula (III) may be prepared by standard methods of peptide synthesis, for example, solid-phase peptide synthesis (see e.g. Atherton, E. and Sheppard, R. C.; "Solid Phase Synthesis"; IRL Press: Oxford, 1989). Incorporation of the primary amine group in a compound of formula (III) may be achieved by reaction of the N or C-terminus of the peptide or with some other functional group contained within the peptide sequence, modification of which does not affect the binding characteristics of the vector. The primary amine group is preferably introduced by formation of a stable amide bond formed by reaction of a peptide amine function with an activated acid and introduced either during or following the peptide synthesis. When the precursor is an acid then the primary amine can be introduced using in situ activating agents such as 2-(1H-benzotriazole-1-yl)-1,1,3,3-tetramethyluronium hexafluorophosphate (HBTU) or N-[(dimethylamino)-1H-1,2,3-triazolo[4,5-b]pyridin-1-ylmethylene]-N-methylmethanaminium hexafluorophosphate N-oxide (HATU).

In another embodiment the radiofluorination process of the present invention further comprises the step of reacting the compound of formula (II) with a compound of formula (A):

wherein R" denotes a $C_{1-3}$ alkyl group optionally substituted by a group —N(R''')$_2$ and wherein each R''' group is independently selected from $C_{1-3}$ alkyl and H.

Preferably in such embodiments of the invention the compound of formula (II) is a compound in which the group R is —COOR' as described herein, such that the compound of formula (II) is a compound of formula (IIi), (IIj), (IIk) or (III) as described herein.

Reaction of a compound of formula (II) with a compound of formula (A) therefore provides a compound of formula (B):

A preferred group —N(R''')$_2$ is —N(CH$_2$CH$_3$)$_2$. A particularly preferred compound of formula (A) is N,N-diethyleneethylenediamine: H$_2$NCH$_2$CH$_2$N(CH$_2$CH$_3$)$_2$. Thus, preferred compounds of formula (B) are those of formula (BB):

A particularly preferred compound of formula (BB) is [¹⁸F]MEL050:

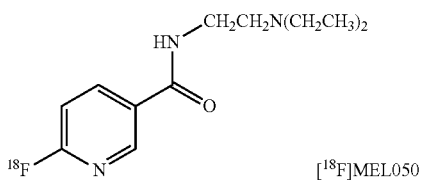

[¹⁸F]MEL050 may for example be obtained by reacting [¹⁸F]F-Py-TFP with N,N-diethyleneethylenediamine. This may be carried out after synthesis of [¹⁸F]F-Py-TFP in accordance with the methods of the invention. [¹⁸F]MEL050 is particularly useful as a melanoma tracer.

Certain compounds of formula (B) and formula (BB) are themselves novel and therefore in a further embodiment the present invention provides compounds of formula (B), preferably of formula (BB), as described herein, with the proviso that the compound is not [¹⁸F]MEL050.

Precursor compounds of formula (I) and salts thereof may be prepared from commercially available starting materials. Where the group R is an ester (—COOR') the precursor compound may for example be prepared by reacting a carboxylic acid of formula (V) with an alcohol of formula R'—OH (where R' has the meaning as herein described) under standard esterification conditions, for example in the presence of N,N'-Dicyclohexylcarbodiimide or an acid catalyst such as sulphuric acid:

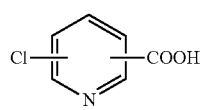
(V)

followed by nucleophilic aromatic substitution of the Cl substituent using a precursor of L such as trimethylamine (where L is —NMe₃⁺), 4-diazabicyclo[2.2.2]octane (where L is DABCO) or N-methyl pyrrolidine (where L is 1-methyl-pyrrolidin-1-ium). The nucleophilic aromatic substitution may typically be performed using THF as the solvent.

The preparation of N,N,N-trimethyl-5-((2,3,5,6-tetrafluorophenoxy)-carbonyl)pyridin-2-aminium trifluoromethanesulfonate starting from 6-chloronicotinic acid is described in Olberg et al. (Journal of Medicinal Chemistry, 53, 1732-1740 (2010)). Other compounds of general formula (I) where R is —COOR' may be prepared analogously.

Where the group R is an aldehyde (—CHO) the precursor compound may for example be prepared by reacting an aldehyde of formula (VI) with a precursor of L such as trimethylamine (where L is —NMe₃⁺) or N-methyl pyrrolidine (where L is 1-methyl-pyrrolidin-1-ium) in a nucleophilic aromatic substitution reaction:

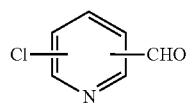
(VI)

The process according to the invention relates to synthesis methods for labelling compounds with the positron emitter fluorine-18 which may be used in positron emission tomography (PET) imaging. Therefore in a further embodiment the present invention provides a positron emission tomography imaging method comprising the following steps:
(a) preparing a compound of formula (II) by the radiofluorination process as herein described;
(b) reacting the compound of formula (II) with a compound of formula (III) as herein described whereby to provide a radiolabelled biomolecule of formula (IV) as herein described;
(c) administering said radiolabelled biomolecule of formula (IV) to a human or animal (e.g. mammalian) subject; and
(d) acquiring a PET image of said subject.

In a further embodiment the present invention provides a positron emission tomography imaging method comprising acquiring a PET image of a human or animal (e.g. mammalian) subject to whom a radiolabelled biomolecule of formula (IV) as herein described has been administered.

The administration of the biomolecule of formula (IV) is preferably performed by intravenous administration. The PET image may be acquired using any conventional PET imaging apparatus.

PET imaging is a powerful diagnostic tool in many branches of medicine and can be used to assist in the diagnosis of diseases and conditions including, but not limited to, cancer (e.g. in Hodgkin's lymphoma, prostate cancer, breast cancer, clear cell renal cell carcinoma, non-Hodgkin lymphoma, lung cancer, adrenocortical tumours, and pheochromocytoma); neurological diseases such as Alzheimer's disease; neuropsychiatric conditions such as schizophrenia or mood disorders; cardiological diseases such as hibernating myocardium or atherosclerosis; or infectious diseases. Thus in a further embodiment the present invention provides a method of diagnosis comprising performing a PET imaging method as herein described and making a diagnosis on the basis of the acquired PET image. The diagnosis may desirably be a diagnosis of any of the aforementioned diseases or conditions.

PET imaging (including the PET imaging methods of the invention) can also be employed for non-diagnostic purposes such as the study of pharmacokinetics, neuropsychology, and musculoskeletal imaging.

The PET image acquired in the imaging methods and/or method of diagnosis according to the invention can, for example, be an image of the whole body, the brain, bone, the lungs, the heart, the digestive system, the musculoskeletal system, the vascular system, the liver, the kidneys, or the lymphatic system, or any combination or portion thereof.

Certain precursor compounds of formula (I) and their corresponding radiofluorinated derivatives (prosthetic groups) are themselves new and form further aspects of the invention.

In another aspect the present invention thus provides a compound of formula (I'):

(I')

(wherein L is as hereinbefore defined), optionally in the form of a salt with a suitable counterion as hereinbefore described, such as a chloride, bromide, phosphate, metaphosphate, perchlorate, nitrate, sulphate, tartrate, trifluoroacetate, citrate, malate, lactate, fumarate, benzoate, glycolate, gluconate, succinate, methanesulphonate, trifluoromethanesulphonate, or para-toluenesulphonate anion.

Compounds of formulae (Ie), (If), (Ig) and (Ih) are all compounds of formula (I'). Such compounds and their salts with a suitable counterion (such as those herein described) form a further aspect of the invention.

In an embodiment the compound of formula (I') is a 5-formyl-N,N,N-trimethylpyridin-2-aminium salt, e.g. the trifluoromethanesulfonate salt.

Other novel compounds of formula (I) include those of formula (I"):

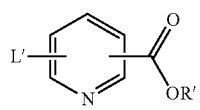

(I")

(where R' is as hereinbefore defined and L' is 1,4-diazabicyclo[2.2.2]octan-1-ium or 1-($C_{1-3}$ alkyl)-pyrrolidin-1-ium, e.g. 1-methyl-pyrrolidin-1-ium), optionally in the form of a salt with a suitable counterion as hereinbefore described such as a chloride, bromide, phosphate, metaphosphate, perchlorate, nitrate, sulphate, tartrate, trifluoroacetate, citrate, malate, lactate, fumarate, benzoate, glycolate, gluconate, succinate, methanesulphonate, trifluoromethanesulphonate, or para-toluenesulphonate anion.

In an embodiment the compound of formula (I") is a compound of formula (Im")

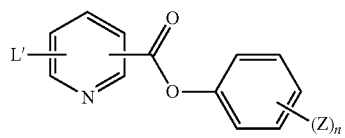

(Im")

(wherein L', Z and n have the meanings described above), optionally in the form of a salt with a suitable counterion as hereinbefore described such as a chloride, bromide, phosphate, metaphosphate, perchlorate, nitrate, sulphate, tartrate, trifluoroacetate, citrate, malate, lactate, fumarate, benzoate, glycolate, gluconate, succinate, methanesulphonate, trifluoromethanesulphonate, or para-toluenesulphonate anion.

In another embodiment the compound of formula (I") is a compound of formula (In"):

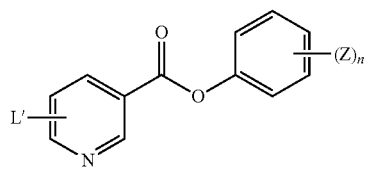

(In")

(wherein L', Z and n have the meanings described above), optionally in the form of a salt with a suitable counterion as hereinbefore described such as a chloride, bromide, phosphate, metaphosphate, perchlorate, nitrate, sulphate, tartrate, trifluoroacetate, citrate, malate, lactate, fumarate, benzoate, glycolate, gluconate, succinate, methanesulphonate, trifluoromethanesulphonate, or para-toluenesulphonate anion.

In an embodiment the compound of formula (I") is a 1-methyl-1-(5-((2,3,5,6-tetrafluorophenoxy)carbonyl)pyridin-2-yl)pyrrolidin-1-ium salt, e.g. the trifluoromethanesulfonate salt.

The [$^{18}$F]fluoro-substituted compounds of formula (II) which are obtained by reaction of the new compounds of formula (I') with [$^{18}$F]fluoride anions are themselves also new and form part of the invention. Thus in another aspect the invention provides a radiofluorinated compound of formula (II'):

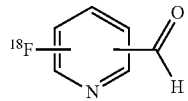

(II')

In an embodiment the compound of formula (II') is 6-[$^{18}$F]fluoropyridine-3-carboxaldehyde.

The radiofluorinated analogs of compounds of formula (Im") and (In") also form part of the invention.

Methods for the preparation of any of the novel compounds herein described, including methods for radiofluorination of any of the precursor compounds, also form part of the invention. Methods for preparing such compounds and for performing radiofluorination are as described above.

Methods for preparing a radiofluorinated biomolecule comprising the step of reacting any of the novel radiofluorinated compounds (prosthetic groups) with a compound of formula (III) as defined herein form a further aspect of the invention. The resulting labelled biomolecules also form part of the invention as do their use as radiopharmaceuticals, for example in PET imaging methods.

The invention will now be illustrated by means of the following non-limiting Examples and the attached Figures in which.

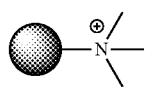

denotes a solid phase support with anion exchange properties.

Figure 3:
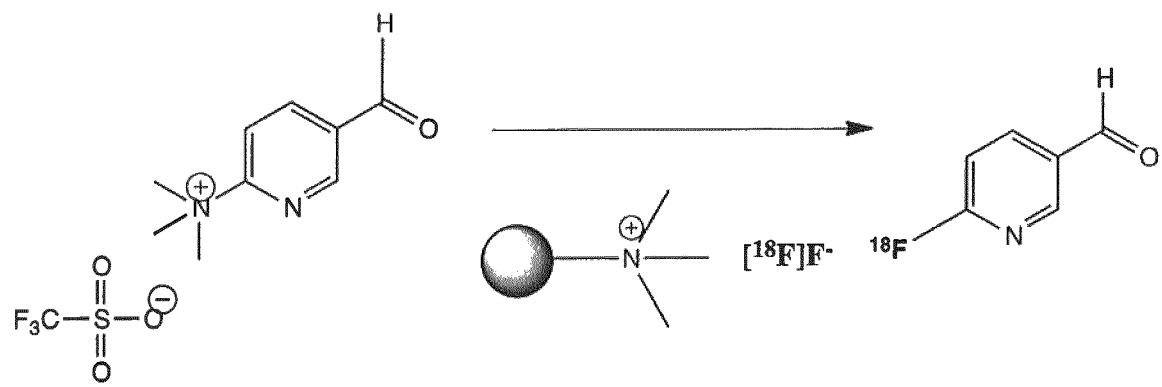

FIG. 3 shows a non-limiting schematic of a reaction process for producing an [$^{18}$F]fluorinated compound starting from a precursor having an aldehyde substituent in accordance with the invention.

EXAMPLE 1

Experimental

Chemicals and solvents of reagent grade obtained commercially were of a purity of 95% and were used without further purification. Water (ultra-pure, ion-free) was obtained from a Millipore Ultra-pure water system. HPLC solvents were obtained from Merck KGaA (VWR). Synthesis of 6-fluoronicotinic acid 2,3,5,6-tetrafluorophenyl ester (F-Py-TFP) and N,N,N-trimethyl-5-((2,3,5,6-tetrafluorophenoxy)-carbonyl)pyridin-2-aminium trifluoromethanesulfonate was performed as previously reported by Olbeg et al. (J. Med. Chem, 53: 1732-1740).

Radiochemistry: Radiochemical synthesis was performed manually behind lead shield using aqueous [$^{18}$F]fluoride obtained from a cyclotron (GE PETtrace 6) using $^{18}$O(p,n) $^{18}$F nuclear reaction with a 16.5 MeV proton irradiation. Typically experiments were conducted with 30 to 62 MBq of $^{18}$F starting radioactivity.

Analytical HPLC was performed on an Agilent system (1200 series) with UV detection at 214 and 254 nm in series with a γ-detector (Raytest GABI Star 1207 radiometric detector, Straubenhardt, Germany) equipped with C-18 reversed-phase column (ACE analytical 4.6×50, 5µ) using a gradient of 10-95% solvent B in water/0.1% TFA over 10 min with a flow rate of 1.0 mL/min. EZchrome software was used to record and analyze both UV and radiometric data. Radio-TLC was recorded using a Gina Star TLC and analyzed using the Raytest miniGita software (Straubenhardt, Germany). Acetonitrile was used as the mobile phase. Radioactivity was assayed using a calibrated Capintec CRC-15R dose calibrator (Ramsey, N.J., USA)

Experiment 1

31.3 MBq of [$^{18}$F]fluoride obtained from an aqueous solution was trapped on Chromafix/Chromabond PS—$CO_3^-$ anion exchange column (type shorty, MACHEREY-NAGEL GmbH & Co. KG, Düren, Germany). The column was immediately rinsed with 2 mL of dry acetonitrile and purged with air (6 mL with syringe) after which it was incubated at room temperature with a 0.5 ml mixture containing 22.94 mg of N,N,N-trimethyl-5-((2,3,5,6-tetrafluorophenoxy)-carbonyl)pyridin-2-aminium trifluoromethanesulfonate (1 eq.) precursor, 8 µL DIEPA (1 eq.) in 1:1 acetonitrile/t-BuOH for 2 min and 30 seconds before the solution was pushed completely through the column manually with a syringe filled with air into an empty 3 ml glass vessel (receiving vial) and immediately analyzed by radio-TLC and HPLC. The radioactivity in the receiving vial was 20.5 MBq measured in a dose calibrator 9 min after trapping of [$^{18}$F]fluoride (31.3 MBq) on the column. Radio-HPLC showed a major radioactive peak at 254 nm co-eluting with the reference standard, confirming identity, and radio-TLC showed 92.5% radiochemical yield of [$^{18}$F]F-Py-TFP.

Experiment 2

65.1 MBq of [$^{18}$F]fluoride obtained from an aqueous solution was trapped on Chromafix/Chromabond PS—$CO_3^-$ anion exchange column (type shorty, MACHEREY-NAGEL GmbH & Co. KG, Düren, Germany). The column was immediately rinsed with 2 mL of dry acetonitrile and purged with air (6 mL with syringe) after which it was incubated at room temperature with a 0.5 ml mixture containing 30 mg of N,N,N-trimethyl-5-((2,3,5,6-tetrafluorophenoxy)-carbonyl)pyridin-2-aminium trifluoromethanesulfonate (1 eq.) precursor, 14 µL triethylamine (1.5 eq.) in 1:1 acetonitrile/t-BuOH for 2 min and 30 seconds before the solution was pushed completely through the column manually with a syringe filled with air into an empty 3 ml glass vessel (receiving vial) and analyzed by radio-TLC and HPLC. The radioactivity in the receiving vial was 40.5 MBq measured in a dose calibrator 10 min after trapping of [$^{18}$F]fluoride (65.1 MBq) on the column. Radio-HPLC showed a major radioactive peak co-eluting with the reference standard (Rt=7.9 min), confirming identity, and radio-TLC showed 95% radiochemical yield of [$^{18}$F]F-Py-TFP.

EXAMPLE 2

Experimental

Chemicals and solvents of reagent grade were obtained as detailed in Table 3 and were used without further purification. Water (ultra-pure, ion-free) was obtained from a Millipore Ultra-pure water system. HPLC solvents were obtained from Merck KGaA (VWR).

Radiochemistry, analytical HPLC, radio-TLC and radioactivity assays were performed as described in the Experimental section of Example 1.

TABLE 3

| Chemical/Solvent | Supplier | Cat. No | Grade | Lot/Batch | MW | d (g/ml) | R | S |
|---|---|---|---|---|---|---|---|---|
| THF | Alfa Aesar | A12686 | 97% | 10181607 | NA | | 36/37/38 | 26-36 |
| Dichloromethane | Fluka | 66749 | Puriss | 1208726 | | | 40 | 23-24/25-36/37 |
| 1M trimethylamine in THF | Acros | 388371000 | | A0338939 | NA | | | |
| Trimethylsilyl trifluoromethane sulfonate (TMSOTf) | Aldrich | 225649 | | | 222.26 | 1.228 | | |
| 6-chloropyridine-3-carboxaldehyde | Aldrich | 596175 | 96% | MKBF5178 | 141.56 | | | |

Synthesis of 5-formyl-N,N,N-trimethylpyridin-2-aminium trifluoromethanesulfonate To a solution of 6-chloropyridine-3-carboxaldehyde (700 mg, 4.9 mmol) in THF (5 ml) was added 1 M trimethylamine solution in THF (10.0 mL). The reaction was stirred overnight at room temperature during which a white precipitate formed.

The precipitate (ammonium chloride salt) was filtered off and washed well with dichloromethane and diethyl ether and dried (Yield: 460 mg, 2.3 mmol). Under an $N_2$ atmosphere the ammonium salt was suspended in dichloromethane (DCM) (50 ml) cooled on an ice bath and TMSOTf (0.5 mL, 2.5 mmol) was added under vigorous stirring. The reaction was allowed to proceed for 30 min on ice after which it was allowed to reach room temperature. When the solid was completely solubilized in the DCM, the organic phase was removed under vacuum. The solid was taken up in acetonitrile (ACN) and filtered and the filtrate was again taken and treated under vacuum to dryness. The solid was precipitated in diethyl ether and filtered off. The solid was dried under high vacuum for two hours. Yield: 0.656 g, 2.1 mmol (43%) (Faint yellowish solid).

NMR analysis confirmed the successful synthesis with the following peaks:

$^1$H NMR (400 MHz, CD$_3$CN): δ 1.19 (s, 1H), δ 9.07 (d, J=1.8 Hz, 1H), δ 8.56 (dd, J$_1$=2.2 Hz, J$_2$=8.6 Hz, 1H), 8.04 (d, J=8.6 Hz, 1H), 3.58 (s, 9H).

$^{13}$C NMR (101 MHz, CD$_3$CN): δ 191.40, 151.80, 142.68, 134.65, 117.00, 56.51.

$^{19}$F NMR (376 MHz, CDCl$_3$): δ −74.03.

Radiolabeling on Solid Phase of 5-formyl-N,N,N-trimethylpyridin-2-aminium trifluoromethanesulfonate with [$^{18}$F]fluoride 47.2 MBq of [$^{18}$F]fluoride obtained from an aqueous solution was trapped on a Chromafix/Chromabond PS—CO$_3^-$ anion exchange column (type shorty, MACHEREY-NAGEL GmbH & Co. KG, Düren, Germany). The column was immediately rinsed with 2 mL of dry acetonitrile and purged with air (6 mL with syringe) after which it was incubated at room temperature with a 0.5 ml mixture containing 20.3 mg of 5-formyl-N,N,N-trimethylpyridin-2-aminium trifluoromethanesulfonate in 1:1 acetonitrile/t-BuOH for 5 minutes before the solution was pushed completely through the column manually with a syringe filled with air into an empty 3 ml glass vessel (receiving vial) and immediately analyzed by HPLC. The radioactivity in the receiving vial was 15.6 MBq measured in a dose calibrator 10 min after trapping of [$^{18}$F]fluoride (47.2 MBq) on the column. Radio-HPLC (ACE 3 C18-50*4.6 mm, 5-50% acetonitrile over 10 min in water/0.05% TFA, 1 ml/min) of eluate showed a major radioactive peak eluting at 3.2 min vs. 1.4 min for precursor. A sample from the receiving vial spiked with reference standard, 6-fluoropyridine-3-carboxaldehyd (t$_R$=3.16 min), confirmed the identity of the radioactive product using the same above stated HPLC conditions.

Purification of the Synthesized 6-[$^{18}$F]fluoropyridine-3-carboxaldehyde

The SPE column used was Sep-Pak Oasis™ MCX plus (Waters) (strong cation exchange/with reversed phase properties for trapping unreacted precursor). Conditioning of the SPE column was performed by using 5 mL EtOH then 5 mL MQ water followed by an air purge. The crude reaction product was diluted in water (6 mL) and loaded onto MCX cartridge followed by a 5 mL air purge. The column bound 6-[$^{18}$F]Fluoropyridine-3-carboxaldehyde was eluted off with 1 mL ACN.

8.72 MBq of pure 6-[$^{18}$F]Fluoropyridine-3-carboxaldehyde were obtained from the Oasis MCX cartridge in 1 mL MeCN (19% radiochemical yield, non-decay-corrected, 60 min after start of synthesis). HPLC confirmed removal of the major bulk of the non-reacted precursor from the reaction mixture.

HPLC and Radio-TLC assays performed in accordance with Example 1 confirmed the the purified radiolabelled product, 6-[$^{18}$F]Fluoropyridine-3-carboxaldehyde in a radiochemical purity >95%.

EXAMPLE 3

Synthesis of 1-methyl-1-(5-((2,3,5,6-tetrafluorophenoxy)carbonyl)pyridin-2-yl)pyrrolidin-1-ium trifluoromethanesulfonate Synthesis of 1-methyl-1-(5-((2,3,5,6-tetrafluorophenoxy)carbonyl)pyridin-2-yl)pyrrolidin-1-ium trifluoromethanesulfonate was performed in line with the synthesis of N,N,N-trimethyl-5-((2,3,5,6-tetrafluorophenoxy)-carbonyl)pyridin-2-aminium trifluoromethanesulfonate as previously reported by Olberg et al. (J. Med. Chem, 53: 1732-1740), but employing N-methyl pyrrolidine in place of trimethylamine:

To a stirred solution of 2,3,5,6-tetrafluorophenyl 6-chloronicotinate (500 mg, 2.54 mmol) in 5 ml dry THF was added 1 mL of N-methylpyrrolidine. A white precipitate started to form after 10 minutes and reaction was allowed to proceed overnight. The precipitate was collected and washed with cold Et$_2$O. The solid residue was suspended in CH$_2$Cl$_2$, and TMSOTf (1 mL, 5.29 mmol) was added over 3 min. The mixture was concentrated, and the residue was recrystallized from Et$_2$O to afford 1-methyl-1-(5-((2,3,5,6-tetrafluorophenoxy)carbonyl)pyridin-2-yl)pyrrolidin-1-ium trifluoromethanesulfonate as a white solid (0.70 g, 55%)

The identity of the synthesised product was confirmed by NMR with the following peaks:

$^1$H NMR (400 MHz, Acetonitrile-d$_3$) δ 9.32 (dd, J=2.3, 0.8 Hz, 1H), δ 8.83 (dd, J=8.7, 2.3 Hz, 1H), δ 8.01 (dd, J=8.7, 0.8 Hz, 1H), δ 7.43 (m, 1H), δ 4.23 (n, 2H), δ 4.01 (m, 2H), δ 3.46 (s, 3H), 2.34 (m, 2H), 2.24 (m, 2H).

$^{19}$F NMR (376 MHz, Acetonitrile-d$_3$) δ −79.36 (s), δ −140.36 (m), 6-154.41 (m).

Radiolabeling on solid phase of 1-methyl-1-(5-((2,3,5,6-tetrafluorophenoxy)carbonyl)pyridin-2-yl)pyrrolidin-1-ium trifluoromethanesulfonate:

49.5 MBq of [$^{18}$F]fluoride obtained from an aqueous solution was trapped on a Chromafix/Chromabond PS-CO$_3^-$ anion exchange column (type shorty, MACHEREY-NAGEL GmbH & Co. KG, Düren, Germany). The column was immediately rinsed with 2 mL of dry acetonitrile and purged with air (6 mL with syringe) after which it was incubated at room temperature with a 0.5 ml mixture containing 30.24 mg 1-methyl-1-(5-((2,3,5,6-tetrafluorophenoxy)carbonyl)pyridin-2-yl)pyrrolidin-1-ium trifluoromethanesulfonate and 10 μL triethylamine in 1:1 acetonitrile/t-BuOH for 2.5 minutes before the solution was pushed completely through the column manually with a syringe filled with air into an empty 3 ml glass vessel (receiving vial) and immediately analyzed by HPLC. The radioactivity in the receiving vial was 23.0 MBq measured in a dose calibrator 14 min after trapping of [$^{18}$F]fluoride (49.5 MBq) on the column. Radio-HPLC (ACE 3 C18-50*4.6 mm, 10-90% acetonitrile over 10 min in water/0.05% TFA, 1 ml/min) of the eluate showed a major radioactive peak co-eluting with F-Py-TFP reference standard at 7.890 min.

EXAMPLE 4

Solid-phase labeling experiments were carried out using Chromafix (Chromabond PS—HCO₃) as the stationary phase. Details are shown in Table 4, where:
Column A is the experiment number
Column B is the precursor amount in mg
Column C identifies the solvent and its overall volume in mL; thus, for example, "1:1 t-BuOH/MeCN/0.5" refers to a 1:1 mixture of t-BuOH and MeCN with an overall volume of 0.5 mL
Column D identifies the base
Column E identifies the amount of Chromafix PS—HCO₃ resin employed in mg
Column F identifies the initial radioactivity trapped on the column in MBq
Column G identifies the experiment start time (hh:mm)
Column H identifies the radioactivity in MBq in the vial used to receive the eluted radiolabelled product
Column I identifies the experiment end time (hh:mm)
Column J identifies the reaction yield (%) identified by radio-TLC
Column K identifies the elution efficiency (%)
Column L identifies the total yield (not decay-corrected) in %

TABLE 4

| A | B | C | D | E | F** | G | H | I | J** | K*** | L**** |
|---|---|---|---|---|---|---|---|---|---|---|---|
| 1 | 21 | MeCN/1 | NA | 45 | 62.8 | 14:06 | 22.4 | 14:25 | 63.3 | 35.7 | 22.6 |
| 2 | NA | MeCN/1 + 1 | NA | NA | NA | NA | 23.1 | NA | 79.7 | NA | NA |
| 3 | 41 | MeCN/0.5 | NA | 45 | 64.0 | 15:00 | 25.7 | 15:15 | 88.6 | 40.1 | 35.5 |
| 4 | NA | MeCN/0.5 | NA | 45 | 20.7 | 15:19 | 34.4 | 15:20 | 94.8 | NA | NA |
| 5 | 45.7 | MeCN/1 | NA | 45 | 35.2 | 13:24 | 14.3 | 13:40 | 75.7 | 40.1 | 30.4 |
| 6 | NA | NA | NA | 45 | NA | NA | NA | NA | 81.0 | NA | NA |
| 7 | 24.8 | 1:1 MeOH/MeCN/0.5 | NA | 45 | 37.5 | 14:27 | 32.9 | 14:26 | 0 | 91.4 | 0 |
| 8 | 21 | 1:1 t-BuOH/MeCN/0.5 | NA | 45 | 36.0 | 15:31 | 2.19 | 15:38 | 95.3 | 60.8 | 57.9 |
| 9 | NA | NA | NA | NA | NA | NA | NA | NA | 98.4 | 60.8 | NA |
| 10 | 23 | 1:1 t-BuOH/MeCN/0.5 | NH₄OTf | 45 | 47.9 | 11:18 | 12.5 | 11:27 | 17.0 | 26.1 | 4.4 |
| 11 | 22 | 8:2 t-BuOH/MeCN/0.5 | NA | 45 | 25.9 | 11:43 | 11.4 | 11:51 | 89.6 | 44.0 | 39.4 |
| 12 | 40 | 1:1 t-BuOH/MeCN/1 | NA | 25 | 41.7 | 13:55 | 20.3 | 14:05 | 87.7 | 48.7 | 42.7 |
| 13 | 20 | 1:1 t-BuOH/MeCN/0.5 | NA | 45 | 29.5 | 14:15 | 8.7 | 14:22 | 90.2 | 29.5 | 26.6 |
| 14 | 20 | 1:1 t-BuOH/MeCN/0.5 | NA | 45 | 40.6 | 15:38 | 18.8 | 15:47 | 81.8 | 46.3 | 37.9 |
| 15 | 40 | 1:1 t-BuOH/MeCN/0.5 | NA | 45# | 27.5 | 11:50 | 9.6 | 12:00 | 76.8 | 34.9 | 26.8 |
| 16 | 40 | 1:1 t-BuOH/MeCN/0.5 | NA | 10 | 27.2 | 12:26 | 12.1 | 12:33 | NA | 44.5 | NA |
| 17 | 22 | 1:1 t-BuOH/MeCN/0.5 | NA | ## | 33.6 | 13:27 | 0.3 | 13:33 | NA | 0.9 | NA |
| 18 | 23 | 1:1 t-BuOH/MeCN/0.5 | DIPEA 8 µL | 45 | 30.9 | 14:19 | 20.5 | 14:26 | 92.5 | 66.3 | 61.3 |
| 19 | 23 | 1:1 t-BuOH/MeCN/0.5 | DIPEA 8 µL + TBAOTf | 45 | 22.5 | 15:12 | 15.2 | 15:19 | 78.7 | 67.6 | 53.2 |
| 20 | 15 | 1:1 t-BuOH/MeCN/0.5 | NA | 45 | NA | NA | NA | NA | NA | NA | NA |
| 21 | 20 | 1:1 t-BuOH/MeCN/0.5 | DIPEA 5 µL | 45 | 23.2 | 14:17 | 8.7 | 14:24 | NA | 37.5 | NA |
| 22 | 24 | 1:1 t-BuOH/MeCN/0.5 | DIPEA 10 µL | 45 | 16.2 | 14:53 | 10.0 | 14:59 | NA | 61.7 | NA |
| 23 | 23 | 1:1 t-BuOH/MeCN/0.5 | DIPEA 12 µL | 45 | 43.4 | 15:19 | 29.3 | 15:26 | 70.7 | 67.5 | 47.7 |
| 24 | 20 | 1:1 t-BuOH/MeCN/0.5 | TEA 6 µL | 45 | 44.6 | 15:32 | 24.6 | 15:40 | NA | 55.2 | NA |
| 25 | 30 | 1:1 t-BuOH/MeCN/0.5 | TEA 14 µL | 45 | 63.2 | 14:44 | 40.5 | 14:50 | 95.1 | 64.1 | 61.0 |

TABLE 4-continued

| A | B | C | D | E | F** | G | H | I | J** | K*** | L**** |
|---|---|---|---|---|---|---|---|---|---|---|---|
| 26 | 22 | 1:1 t-BuOH/MeCN/ 0.5 | DIPEA 10 μL | 45 | 28.7 | 11:57 | 15.7 | 12:05 | 66.0 | 54.7 | 37.7 |
| 27 | 22 | 1:1 t-BuOH/MeCN/ 0.5 | TEA 10 μL | 45 | 24.3 | 12:17 | 13.7 | 12:22 | 42.3 | 56.4 | 23.9 |
| 28 | 45 | 1:1 t-BuOH/MeCN 0.5 | TEA 20 μL | 45 | 39.6 | 13:36 | 20.7 | 13:44 | 98.24***** | 52.3 | NA |
| 29 | 23 | 1:1 t-BuOH/MeCN/1 | TEA 20 μL | 45 | 46.2 | 15:03 | 27.4 | 15:13 | 36.7 | 59.3 | 21.7 |

NA = not applicable
*After rinsing column with MeCN
**Mobile phase 100% MeCN (some hydrolysis of ester may occur during drying of TLC strip (silica), and actual yield may be under estimated depending on hold-up time of sample on strip)
***Elution efficiency is not corrected for decay and therefore slightly underestimated depending on time between measurements
****RCY by radio-TLC multiplied by elution efficiency
*****Purity after C18 Sep-Pak purification. 16.2 MBq eluted in 1 ml diethyl ether (13:55) from column showing 17. MBq at 13:51, 0.81 MBq remaining on column at 13:56
conditioned with KOTf 0.2M
Waters QMA resin 10 mg Comments to Entries in Table 4:
1. Eluted over 10 minutes (500+200+300). 2 mL MeCN followed by 110 sec He 1000 mL/min
2. Column from 1 re-eluted with additional 1 mL neat MeCN to reaction mixture of entry 1 and heated at 40° C. for 10 min
3. Column treated with He-gas for 120 sec after wash with MeCN. 10 min incubation of precursor mixture on column
4. Same column from 3 re-treated with 0.5 of precursor mix (41 mg/mL) and 10 min incubation, eluted to mixture of 3—elution mix heated to 40° C. for 10 min. Some radioactivity lost to sampling.
5. Elution done in steps over 5 min—pulling Rx back and forth over column.
6. Same as 5 heated to 50° C. for 10 min
7. 2 min soak—no Rx.
8. 2 min and 30 sec soak. (2 ml MeCN rinse before Rx)—remaining 12.7 MBq on column at 15:37
9. Same 9 reaction mixture heated to 40° C. for 5 min
10. 2 min and 30 sec soak. 60 μL of 1M NH₄OTf added to elution mixture (Triflate salt acidic—impurities can be adjusted with base)
11. 2 min and 30 sec soak
12. Elution mix pushed in steps over 5 min. Pressure was also applied to column when eluting
13. Elution mix pushed in steps over 5 min
14. 250 μL of precursor eluent pushed through column and column heated in Scansys reactor at 60° C. for 5 min before eluting with last 250 μL of precursor eluent
15. i) Cartridge washed with 10 mL MQ water
    ii) Conditioning with KOTf$_{(aq)}$ (0.2 M) 10 mL
    ii) Wash with water—10 mL
    Rx with precursor mixture in two steps—where elution mix is reintroduced over column a 2$^{nd}$ time (only final result reported). 1 mL of 0.9% NaCl releases remaining activity on column
16. 0.5 MBq bleed through column (12:32). Dropwise elution over 2 min. No effect of re-elution with reaction mixture
17. Rx—with silica based anion-exchange resin. 2 min and 30 sec soak. Practically no activity eluted off column
18. Non-nucleophilic base added to elution mixture. 2 min and 30 sec soak. No apparent precipitation after 30 min
19. TBA-OTf in t-BuOH/MeCN 1:1 20 μL added to precursor mixture. 2 min and 30 sec soak
20. Added 10 μL of 0.9% NaCl to elution mixture. Only 10% activity off column
21. Column rinse with only 1 mL acetonitrile. 2 min and 30 sec soak
22. 2 min and 30 sec soak. Column rinse with only 2 mL acetonitrile
23. 2 min and 30 sec soak. Column rinse with only 2 mL acetonitrile
24. New batch of Chromabond PS—HCO₃ columns. 2 min and 30 see soak. Column rinse with only 2 mL acetonitrile
25. Chromabond not conditioned with water before use, incubated with MeCN for 30 min before use
26. No conditioning of column, observed no bleed through of fluoride. Soak with MeCN (5 min) after trapping fluoride. Column rinse with only 2 mL acetonitrile
27. MeCN conditioning of column (5 min), no bleed through of fluoride. Column rinse with only 2 mL acetonitrile (as normally done). 2 min and 30 sec soak
28. 2 min and 30 sec soak. Crude loaded onto C18 Sep-Pak after diluting with 5 ml 2% acetic acid solution, rinsed with water (5 mL) and eluted off with diethyl ether (1 mL)
29. Column conditioned with water and then 5 min soak with MeCN before use

EXAMPLE 5

Solid-phase labeling experiments were carried out using various different resins as the stationary phase. Chromafix (Chromabond PS—HCO₃), as employed in Example 4, was used as a control (entry 3 in the table). Details are shown in Table 5, where Columns A-D and F-L denote the same meanings as in Example 4. Column E identifies the type and amount of anion exchange resin employed in mg, with bicarbonate as the counterion.

TABLE 5

| A | B | C | D | E | F* | G | H | I | J** | K*** | L**** |
|---|---|---|---|---|----|---|---|---|-----|------|-------|
| 1 | 30 | 1:1 t-BuOH/ MeCN/0.5 | TEA (14 μL) | Bakerbond XWP 500 PolyQuat-35/41 mg | 22.7 | 12:22 | 5.6 | 12:32 | NA# | 24.7 | NA |
| 2 | 30 | 1:1 t-BuOH/ MeCN/0.5 | TEA (14 μL) | Waters Oasis MAX resin/43 mg | 27.4 | 12:46 | 15 | 12:54 | 70.0 | 56.6 | 39.6 |
| 3 | 30.4 | 1:1 t-BuOH/MeCN/ 0.5 | TEA (14 μL) | Chromabond- PS HCO3- 45 mg | 28.3 | 13:15 | 17.7 | 15:23 | 95.8 | 62.5 | 59.9 |
| 4 | 22 | 1:1 t-BuOH/MeCN/ 0.5 | NA | Waters QMA resin/ 10 mg | 32.3 | 13:24 | 0.3 | 13:33 | NA | 0.93 | NA |

= poor elution.

*After rinsing column with MeCN

**Mobile phase 100% MeCN (some hydrolysis of ester may occur during drying of TLC strip (silica), and actual yield may be under estimated depending on hold-up time of sample on strip)

***Elution efficiency is not corrected for decay and therefore slightly underestimated depending on time between measurements

****RCY by radio-TLC multiplied by elution efficiency

Comments to Entries in Table 5:

30. 2 min and 30 sec soak. Column rinse with only 2 mL acetonitrile. HPLC confirms product in high radiochemical purity. (Polymer based)

31. 2 min and 30 sec soak. Column rinse with only 2 mL acetonitrile. HPLC and TLC confirms product in high radiochemical purity. (Polymer based)

32. 2 min and 30 sec soak. Column rinse with only 2 mL acetonitrile (as normally done). HPLC and TLC confirms product in high radiochemical purity. (Polymer based)

33. Practically no elution using Waters QMA resin (silica based)

EXAMPLE 6

Figure 1:
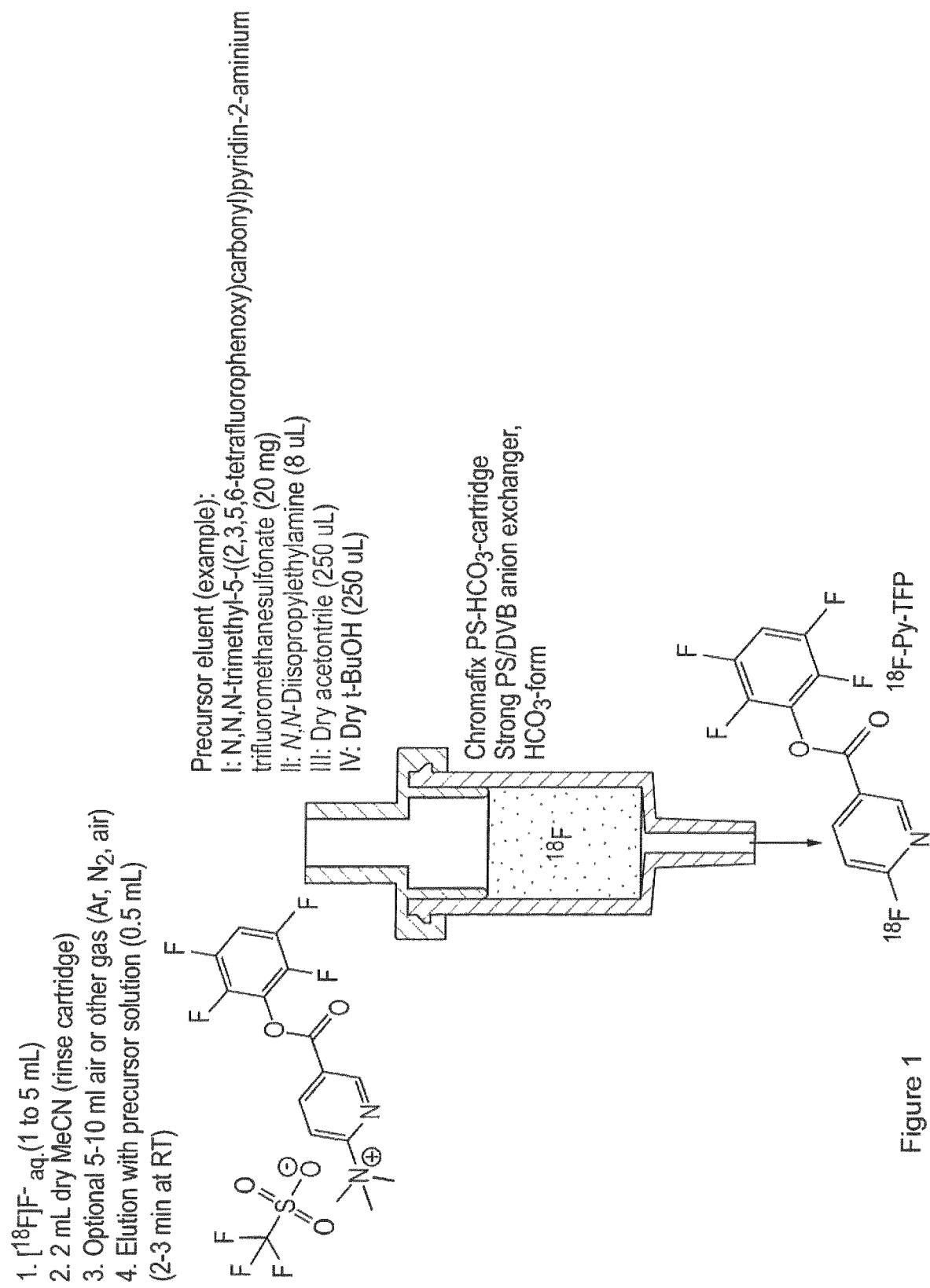
FIG. 1 shows a schematic for the preparation of [$^{18}$F]F-Py-TFP in accordance with the invention as described in non-limiting Example 6.
Figure 2:
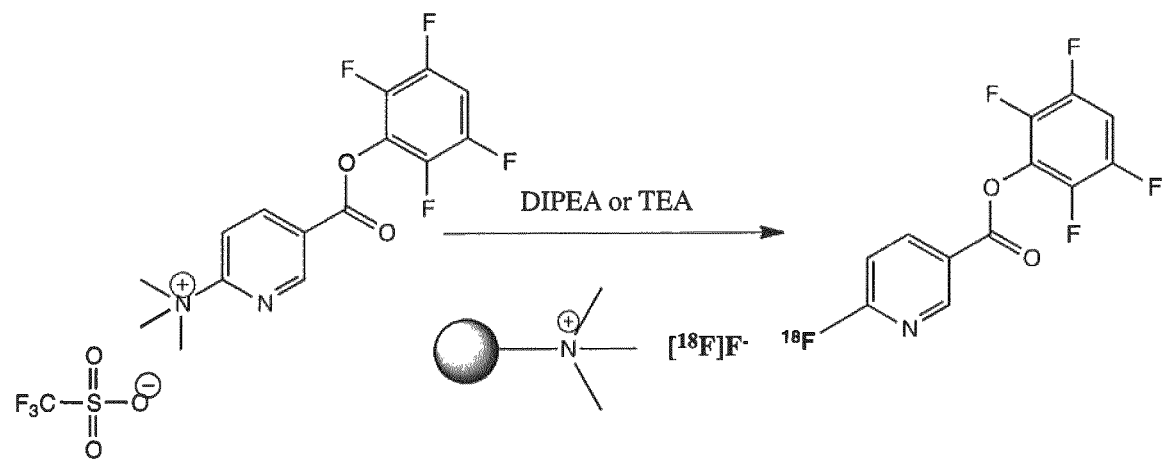
FIG. 2 shows a non-limiting schematic of a reaction process for producing [$^{18}$F]F-Py-TFP in accordance with the invention, where.

FIG. 1 shows a schematic example of the synthesis of [$^{18}$F]F-Py-TFP using the process of the invention. A Chromafix PS—HCO$_3^-$ cartridge (a strong PS/DVB anion exchanger in HCO$_3^-$-form) is loaded with 1 to 5 mL of aqueous [$^{18}$F]F$^-$. The cartridge is dried by rinsing with 2 mL dry acetonitrile and then 5-10 ml of air.

20 mg of precursor (N,N,N-trimethyl-5 [(2,3,5,6-tetrafluorophenoxy)carbonyl]pyridin-2-aminium trifluoromethanesulfonate) in 8 μl N,N-diisopropylethylamine are eluted through the column for 2 to 3 minutes at room temperature. Following the elution of the precursor the cartridge is rinsed with 250 μl dry acetonitrile and 250 μl dry t-BuOH. [$^{18}$F]F-Py-TFP is recovered in good yield.

EXAMPLE 7

Radioabelling of 5-(((1,1,1,3,3,3-hexafluoropropan-2-yl)oxy)carbonyl)-N,N,N-trimethylpyridin-2-aminium trifluoromethanesulfonate

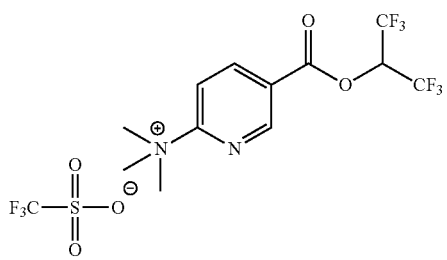 [SMILES: O=S(=O)([O-])C(F)(F)F ; C[N+](C)(C)c1ccc(C(=O)OC(C(F)(F)F)C(F)(F)F)cn1]

5-(((1,1,1,3,3,3-hexafluoropropan-2-yl)oxy)carbonyl)-N,N,N-trimethylpyridin-2-aminium trifluoromethanesulfonate Experimental Preparation of 1,1,1,3,3,3-hexafluoropropan-2-yl 6-chloronicotinate To a stirred solution of 6-chloronicotinic acid (500 mg, 3.17 mmol) and N,N'-dicyclohexylcarbodiimide (DCC) (648 mg, 3.16 mmol) in tetrahydrofuran (THF) (15 mL) was added 1,1,1,3,3,3-Hexafluoro-2-propanol (HFIP) (401 μL, 3.81 mmol) and a catalytic amount of 4-dimethylaminopyridine (DMAP). The mixture was stirred for 48 h at room temperature. The organic phase was removed in vacuo after which the solid residue was purified by silica gel flash chromatography (hexanes:ethyl acetate 1:1) 1,1,1,3,3,3-hexafluoropropan-2-yl 6-chloronicotinate was obtained as a colourless solid (780 mg, 2.54 mmol).

Preparation of 5-(((1,1,1,3,3,3-hexafluoropropan-2-yl)oxy)carbonyl)-N,N,N-trimethylpyridin-2-aminium trifluoromethanesulfonate 1,1,1,3,3,3-hexafluoropropan-2-yl 6-chloronicotinate (780 mg, 2.54 mmol) was dissolved in 5 ml dry THF after which was added 1 M trimethylamine solution in THF (5.0 mL). A white precipitate was found 10 minutes after the reaction started, which was allowed to proceed overnight. The precipitate was collected and washed with cold $Et_2O$. The solid residue was suspended in $CH_2Cl_2$, and TMSOTf (1 mL, 5.29 mmol) was added over 3 minutes. The mixture was concentrated, and the residue was recrystallized from $Et_2O$ to afford 5-(((1,1,1,3,3,3-hexafluoropropan-2-yl)oxy)carbonyl)-N,N,N-trimethylpyridin-2-aminium trifluoromethanesulfonate as a white solid (0.55 g, 45% yield).

Formation of 5-(((1,1,1,3,3,3-hexafluoropropan-2-yl)oxy)carbonyl)-N,N,N-trimethylpyridin-2-aminium trifluoromethanesulfonate was confirmed by NMR:

$^1$H NMR (400 MHz, Acetonitrile-$d_3$) δ 9.22 (d, J=2.3 Hz, 1H), δ 8.74 (dd, J=8.8, 2.3 Hz, 1H), δ 8.03 (d, J=8.7 Hz, 1H), δ 6.46 (m, 1H), δ 3.58 (s, 9H).

$^{19}$F NMR (376 MHz, Acetonitrile-$d_3$) δ −73.72, δ −79.36.

Radiolabeling on Solid Phase of 5-(((1,1,1,3,3,3-hexafluoropropan-2-yl)oxy)carbonyl)-N,N,N-trimethylpyridin-2-aminium trifluoromethanesulfonate 84.8 MBq of [$^{18}$F]fluoride obtained from an aqueous solution was trapped on a Chromafix/Chromabond PS-CO3- anion exchange column (type shorty, MACHEREY-NAGEL GmbH & Co. KG, Düren, Germany). The column was immediately rinsed with 2 mL of dry acetonitrile and purged with air (6 mL with syringe) after which it was incubated at room temperature with a 0.5 ml mixture containing 31.2 mg of 5-(((1,1,1,3,3,3-hexafluoropropan-2-yl)oxy)carbonyl)-N,N,N-trimethylpyridin-2-aminium trifluoromethanesulfonate in 1:1 acetonitrile/t-BuOH for 2.5 minutes before the solution was pushed completely through the column manually with a syringe filled with air into an empty 3 ml glass vessel (receiving vial) and immediately analyzed by HPLC. The radioactivity in the receiving vial was 48.4 MBq measured in a dose calibrator 10 min after trapping of [$^{18}$F]fluoride (84.8 MBq) on the column. Radio-HPLC (ACE 3 C18-50*4.6 mm, 10-90% acetonitrile over 10 min in water/ 0.05% TFA, 1 ml/min) of eluate showed a major radioactive peak eluting at 7.893 min expected to be 1,1,1,3,3,3-hexafluoropropan-2-yl 6-[$^{18}$F]fluoronicotinate ($^{18}$F-Py-HFIP).

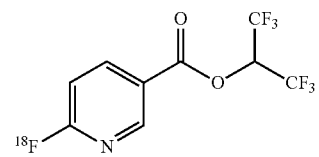 [SMILES: O=C(OC(C(F)(F)F)C(F)(F)F)c1ccc([18F])nc1]

$^{18}$F-Py-HFIP (1,1,1,3,3,3-hexafluoropropan-2-yl 6-[$^{18}$F]fluoronicotinate)

EXAMPLE 8

AG® MP-1M Anion Exchange Resins of mesh size 200-400 and 50-100 (each 42 mg) were weighed out in two empty Chromafix columns (shorty MACHEREY-NAGEL GmbH & Co. KG, Düren, Germany) and converted from chloride form to the $HCO_3^-$ form by passing a 10 mL 1M $KHCO_3$ solution over the resins, followed by 10 mL Milli-Q water and then dried with air. 5 to 10 MBq of [$^{18}$F]fluoride obtained from an aqueous solution was trapped on the AG resins.

The columns were immediately rinsed with 2 mL of dry acetonitrile and purged with air (6 mL with syringe) after which they were incubated at room temperature with a 0.5 ml mixture containing 22.94 mg of N,N,N-trimethyl-5-((2,3,5,6-tetrafluorophenoxy)-carbonyl)pyridin-2-aminium trifluoromethanesulfonate (1 eq.) precursor, 10 L TEA (triethylamine) (1 eq.) in 1:1 acetonitrile/t-BuOH for 2 min and 30 seconds before the solution was pushed completely through the column manually with a syringe filled with air into an empty 3 ml glass vessel (receiving vial) and immediately analyzed by radio-TLC and HPLC. Radio-HPLC showed a major radioactive peak at 254 nm co-eluting with the reference standard, confirming identity, and radio-TLC showed 92.5% radiochemical yield of [$^{18}$F]F-Py-TFP. The radiochemical yields and purities can be found in Table 6.

TABLE 6

BioRad polymer resin solid-phase labeling results of $^{18}$F-Py-TFP

| Entry | A | B | C | D | E | F | G | H | I | J | K | L |
|---|---|---|---|---|---|---|---|---|---|---|---|---|
| 1 | BioRad AG-MP-1M (200-400 mesh) | 30 | C1 | TEA ~10 μL | 42.3 | 8.90 | 16:21 | 5.76 | 16:31 | 76.8 | 65 | 49.8 |
| 2 | BioRad AG-MP-1M (50-100 mesh) | 30 | C2 | TEA ~10 μL | 43.6 | 5.04 | 16:54 | 1.70 | 17:02 | 28.9 | 34 | 9.9 |

Key to Table 6:
A: Resin
B: Precursor amount (mg)
C: Solvent system (ml)
　C1: 1:1 t-BuOHMeCN/0.5
　C2: 1:1 t-BuOH/MeCN/0.5
D: Base
E: Resin amount (mg)
F: Start activity trapped on column (MBq)*
G: Time start (hh:mm)
H: Activity in receiving vial (MBq)
I: Time end (hh:mm)
J: RCY % by radio-TLC**
K: Elution efficiency (%)***
L: Total yield no decay corrected (%)****
* After rinsing column with MeCN
** Mobile phase 100% MeCN (some hydrolysis of ester may occur during drying of TLC strip (silica), and actual yield may be under estimated depending on hold-up time of sample on strip)
*** Elution efficiency is not corrected for decay and therefore slightly underestimated depending on time between measurements
**** RCY by radio-TLC multiplied by elution efficiency D: Base
E: Resin amount (mg)
F: Start activity trapped on column (MBq)*
G: Time start (hh:mm)
H: Activity in receiving vial (MBq)
I: Time end (hh:mm)
J: RCY % by radio-TLC**
K: Elution efficiency (%)***
L: Total yield no decay corrected (%)****
* After rinsing column with EtOH
** Mobile phase 100% MeCN (some hydrolysis of ester may occur during drying of TLC strip (silica), and actual yield may be under estimated depending on hold-up time of sample on strip)
*** Elution efficiency is not corrected for decay and therefore slightly underestimated depending on time between measurements
**** RCY by radio-TLC multiplied by elution efficiency

EXAMPLE 9

40.2 MBq of [$^{18}$F]fluoride obtained from an aqueous solution was trapped on Chromafix/Chromabond PS—$CO_3^-$ anion exchange column (type shorty, MACHEREY-NAGEL GmbH & Co. KG, Düren, Germany). The column was immediately rinsed with 2 mL of dry absolute ethanol and purged with air (2 mL with syringe) after which it was incubated at room temperature with a 0.5 ml mixture containing 31.93 mg of N,N,N-trimethyl-5-((2,3,5,6-tetrafluorophenoxy)-carbonyl)pyridin-2-aminium trifluoromethanesulfonate (1 eq.) precursor, 10 µL DIEPA (1 eq.) in 1:1 acetonitrile/t-BuOH for 2 min and 30 seconds before the solution was pushed completely through the column manually with a syringe filled with air into an empty 3 ml glass vessel (receiving vial) and immediately analyzed by radio-TLC and HPLC. The radioactivity in the receiving vial was 32.4 MBq measured in a dose calibrator 8 min after trapping of [$^{18}$F]fluoride (39.6 MBq) on the column. Radio-HPLC showed a major radioactive peak at 254 nm co-eluting with the reference standard, confirming identity, and radio-TLC showed 28% radiochemical yield of [$^{18}$F]F-Py-TFP.

EXAMPLE 10

97.4 MBq of [$^{18}$F]fluoride obtained from an aqueous solution was trapped on Chromafix/Chromabond PS—$CO_3^-$ anion exchange column (type shorty, MACHEREY-NAGEL GmbH & Co. KG, Düren, Germany). The column was immediately rinsed with 2 mL of dry acetonitrile and purged with air (2 mL with syringe) after which it was incubated with a 0.5 ml mixture containing 31.93 mg of N,N,N-trimethyl-5-((2,3,5,6-tetrafluorophenoxy)-carbonyl)pyridin-2-aminium trifluoromethanesulfonate (1 eq.) precursor, 10 µL TEA (1 eq.) in 1:1 acetonitrile/t-BuOH for 2 min and 30 seconds simultaneously using a heat gun blowing hot air over the cartridge (60-70° C. at surface of cartridge) before the solution was pushed completely through the column manually with an air filled syringe into an empty 3 ml glass vessel (receiving vial) and immediately analyzed by radio-TLC and HPLC. The radioactivity in the receiving vial was 72.4 MBq measured in a dose calibrator 11 min after trapping of [$^{18}$F]fluoride (93.9 MBq) on the column. Radio-HPLC showed a major radioactive peak at 254 nm co-eluting with the reference standard, confirming identity, and radio-TLC showed 92% radiochemical yield of [$^{18}$F]F-Py-TFP.

TABLE 7

Using 1 mL EtOH (abs.) replacing MeCN for removing water from ion-exchange cartridge after trapping $^{18}F^-$

| Entry | A | B | C | D | E | F | G | H | I | J | K | L |
|---|---|---|---|---|---|---|---|---|---|---|---|---|
| 1 | Chromafix PS-CO3- anion exchange column (type shorty) | 31 | C1 | DIPEA –10 µL | 45 | 39.6 | 13:21 | 32.4 | 13:29 | 35 | 81.2 | 28 |

Key to Table 7:
A: Resin
B: Precursor amount (mg)
C: Solvent system (ml)
　C1: 1:1 t-BuOH/MeCN/0.5

TABLE 8

| | With heating using heatgun a 5 cm distance over column for 3 min (60-70 C.°) | | | | | | | | | | |
|---|---|---|---|---|---|---|---|---|---|---|---|
| Entry | A | B | C | D | E | F | G | H | I | J | K | L |
| 1 | Chromafix PS-CO3- anion exchange column (type shorty) | 30 | C1 | DIPEA –10 μL | 45 | 93.9 | 00:00 | 74.2 | 00:11 | 92 | 79 | 72.7 |

Key to Table 8:
A: Resin
B: Precursor amount (mg)
C: Solvent system (ml)
 C1: 1:1 t-BuOH/MeCN/0.5
D: Base
E: Resin amount (mg)
F: Start activity trapped on column (MBq)**
G: Time start (hh:mm)
H: Activity in receiving vial (MBq)
I: Time end (hh:mm)
J: RCY % by radio-TLC**
K: Elution efficiency (%)***
L: Total yield no decay corrected (%)****

EXAMPLE 11

Synthesis and Radiolabelling of 1-methyl-1-(5-((2,3,5,6-tetrafluorophenoxy)carbonyl)pyridin-2-yl)pyrrolidin-1-ium trifluoromethanesulfonate

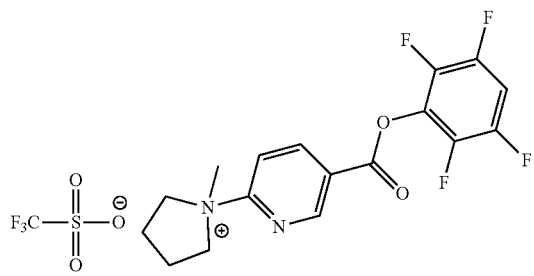 [SMILES: O=S(=O)([O-])C(F)(F)F ; C[N+]1(c2ccc(C(=O)Oc3c(F)c(F)cc(F)c3F)cn2)CCCC1]

Synthesis:

To a stirred solution of 2,3,5,6-tetrafluorophenyl 6-chloronicotinate (500 mg, 2.54 mmol) in 5 ml dry THF was added 1 mL of N-methylpyrrolidine. A white precipitate started to form after 10 min and reaction was allowed to proceed overnight. The precipitate was collected and washed with cold $Et_2O$. The solid residue was suspended in $CH_2Cl_2$, and TMSOTf (1 mL, 5.29 mmol) was added over 3 min. The mixture was concentrated, and the residue was recrystallized from $Et_2O$ to afford 1-methyl-1-(5-((2,3,5,6-tetrafluorophenoxy)carbonyl)pyridin-2-yl)pyrrolidin-1-ium trifluoromethanesulfonate as a white solid (0.70 g, 55%)

$^1H$ NMR (400 MHz, Acetonitrile-$d_3$) δ 9.32 (dd, J=2.3, 0.8 Hz, 1H), δ 8.83 (dd, J=8.7, 2.3 Hz, 1H), δ 8.01 (dd, J=8.7, 0.8 Hz, 1H), δ 7.43 (m, 1H), δ 4.23 (m, 2H), δ 4.01 (m, 2H), δ 3.46 (s, 3H), 2.34 (m, 2H), 2.24 (m, 2H).

$^{19}F$ NMR (376 MHz, Acetonitrile-$d_3$) δ –79.36 (s), δ –140.36 (m), δ –154.41 (m).

Radiolabelling:

49.5 MBq of [$^{18}F$]fluoride obtained from an aqueous solution was trapped on a Chromafix/Chromabond PS-CO3- anion exchange column (type shorty, MACHEREY-NAGEL GmbH & Co. KG, Düren, Germany). The column was immediately rinsed with 2 mL of dry acetonitrile and purged with air (6 mL with syringe) after which it was incubated at room temperature with a 0.5 ml mixture containing 30.24 mg 1-methyl-1-(5-((2,3,5,6-tetrafluorophenoxy)carbonyl)pyridin-2-yl)pyrrolidin-1-ium trifluoromethanesulfonate and 10 μL triethylamine in 1:1 acetonitrile/t-BuOH for 2.5 minutes before the solution was pushed completely through the column manually with a syringe filled with air into an empty 3 ml glass vessel (receiving vial) and immediately analyzed by HPLC. The radioactivity in the receiving vial was 23.0 MBq measured in a dose calibrator 14 min after trapping of [$^{18}F$]fluoride (49.5 MBq) on the column. Radio-HPLC (ACE 3 C18-50*4.6 mm, 10-90% acetonitrile over 10 min in water/0.05% TFA, 1 ml/min) of the eluate showed a major radioactive peak co-eluting with F-Py-TFP reference standard at 7.890 min.

EXAMPLE 12

Radiosynthesis of [$^{18}F$]DCFPyL was carried out according to the protocol described below and illustrated in Scheme 1.

PSMA precursor (Glu-CO-Lys) was obtained from ABX GmBH (Germany).

[$^{18}F$]F-Py-TFP synthesized "on-cartridge" was purified by diluting the downstream eluate (500 μL) with 5 mL 10% AcOH and trapped on a tC18 Sep-Pak Plus cartridge. The cartridge was washed with water (10 mL), and dried with helium-flow. [$^{18}F$]F-Py-TFP was eluted off the C18 cartridge with diethyl ether (2 mL) simultaneously passing the eluate through an $Na_2SO_4$ drying cartridge (Sep-Pak plus long, Waters). The diethyl ether was removed using a helium sweep gas. The purified [$^{18}F$]F-Py-TFP was reconstituted in 500 μL acetonitrile.

To two separate glass vials each containing 1 mg PSMA (Glu-CO-Lys) precursor in 222 uL DMSO was added 2 μL TEA followed by 100 μL of radiochemical pure [$^{18}F$]F-Py-TFP (90 MBq) in MeCN. Reaction was allowed to proceed for 1 h (vial 1) at room temperature and 10 min at 65° C. (vial 2). Radio-HPLC indicated 89% (vial 1) and 85% (vial 2) conversion to [$^{18}F$]DCFPyL. Radiolabeled products co-eluted with an authentic DCFPyL reference sample ($R_T$=3.257 min). Radio-HPLC (ACE 3 C18-50*4.6 mm, 10% ACN in $H_2O$/0.05% TFA isocratic, 5 min, then to 95% ACN over 9 min, 1 ml/min).

Scheme 1

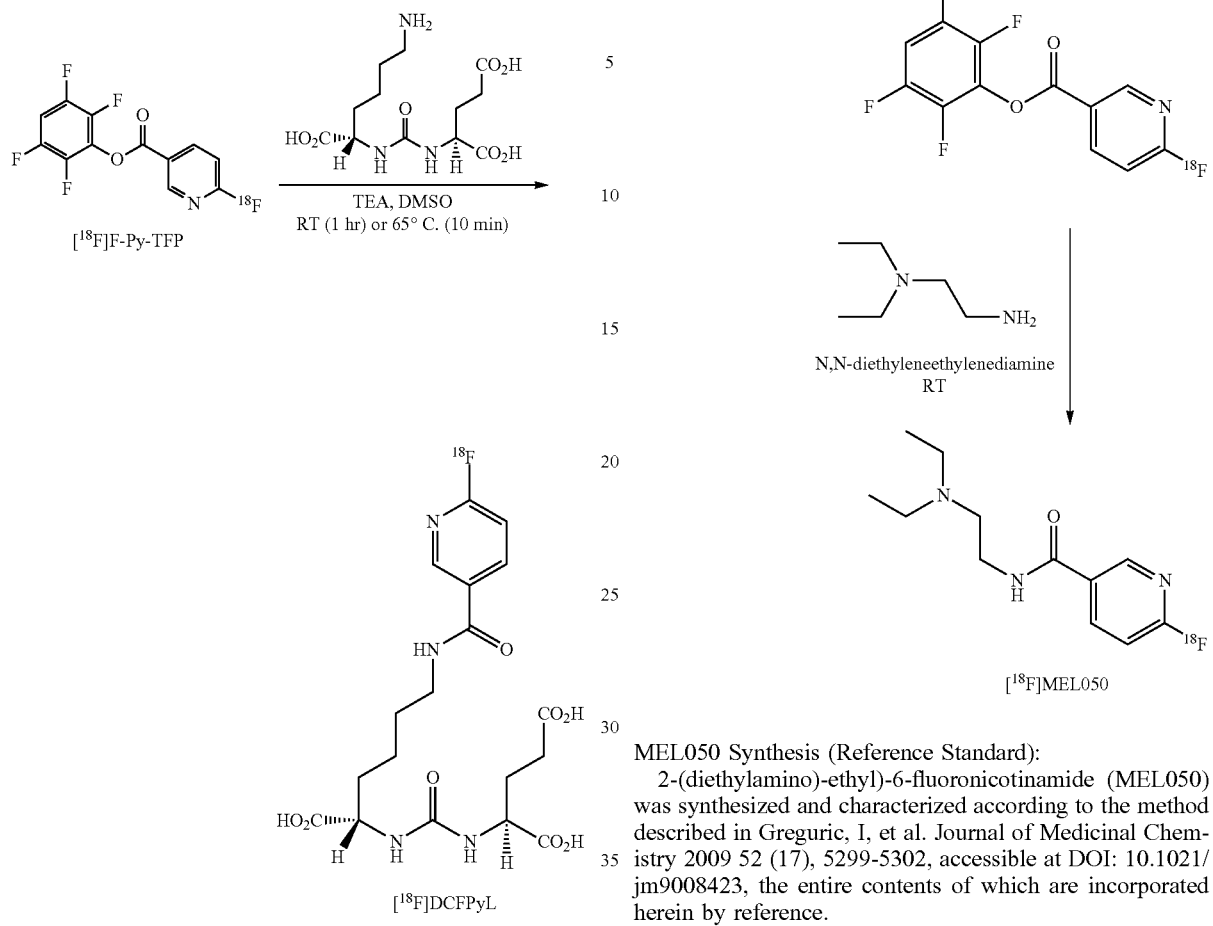

EXAMPLE 13

[$^{18}$F]MEL050 was Synthesised from N,N-diethyleneethylenediamine and $^{18}$F-Py-TFP According to the Protocol Described Below and Illustrated in Scheme 2

Scheme 2

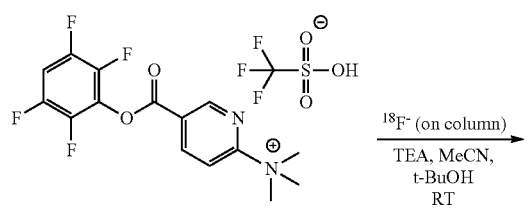

MEL050 Synthesis (Reference Standard):

2-(diethylamino)-ethyl)-6-fluoronicotinamide (MEL050) was synthesized and characterized according to the method described in Greguric, I, et al. Journal of Medicinal Chemistry 2009 52 (17), 5299-5302, accessible at DOI: 10.1021/jm9008423, the entire contents of which are incorporated herein by reference.

[$^{18}$F]MEL050 Synthesis:

21.21 MBq of aqueous fluoride-18 was trapped on Chromafix PS—HCO$_3$ cartridge (type shorty, MACHEREY-NAGEL GmbH & Co. KG, Düren, Germany). The column was immediately rinsed with 2 mL of dry acetonitrile and purged with air (6 mL with syringe) after which it was incubated at room temperature with a 0.5 ml mixture containing 27.6 mg 1-methyl-1-(5-((2,3,5,6-tetrafluorophenoxy)carbonyl)pyridin-2-yl)pyrrolidin-1-ium trifluoromethanesulfonate, 10 µL triethylamine in 1:1 acetonitrile/t-BuOH (500 µL) for 2.5 minutes before the solution was pushed manually and completely through the column with a syringe filled with air into an empty 3 ml glass vessel (receiving vial). The radioactivity in the receiving vial was 16.8 MBq measured in a dose calibrator 8 min after trapping of [$^{18}$F]fluoride (22.21 MBq) on the column.

10 µL N,N-diethyleneethylenediamine was added directly to the receiving vial containing the [$^{18}$F]F-Py-TFP eluate, reacted for 5 min at room temperature and analyzed by radio-TLC and radio-HPLC to verify identity (by co-elution with reference standard) and radiochemical yield. Radio-HPLC and TLC indicated full conversion from [$^{18}$F]F-Py-TFP to [$^{18}$F]MEL050. Free fluoride-18 was removed by trapping the radioactive product after diluting the reaction mixture with water (1:20), loading it onto an Oasis MCX plus cartridge (Waters) followed by a water rinse (5 ml). 7.55 MBq of product was retained on the Oasis MCX plus (Waters) 27 minutes after start of synthesis. A mixture of 5% acetic acid with trimethylamine in water/ethanol (1:1) eluted off radiochemical pure [$^{18}$F]MEL050 (>99% radiochemical purity) in which co-eluted with an authentic reference sample of MEL050 ($R_T$=3.53 min). Radio-HPLC (ACE 3 C18-50*4.6 mm, 3-40% acetonitrile over 10 min in water/ 0.05% TFA, 1 ml/min).

EXAMPLE 14

[$^{18}$F]F-Py-TFP is prepared as described herein and then reacted with biomolecules of general formula (C) in which n is 1, 2, 3, 4, 5, 6, 7, 8 or 9. The reaction is carried out in the presence of TEA and DMSO at room temperature for 1 hour, or at 65° C. for 10 minutes. In an alternative approach the reaction is carried out in the presence of tetraethylammonium bicarbonate and ethanol at 40° C. for 3 minutes.

[$^{18}$F]DCFPyL (where n=4) and analogues with n=1, 2, 3, 5, 6, 7, 8 and 9 are obtained.

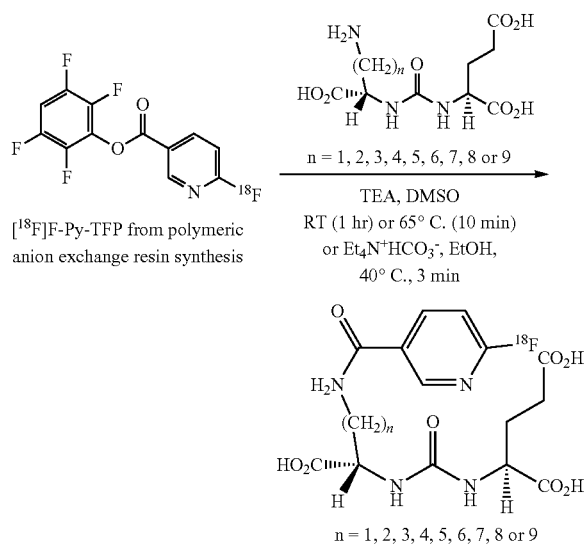

The invention claimed is:

1. A radiofluorination process comprising:
   (a) providing a solid stationary phase which comprises a polymeric anion-exchange resin having bound thereto [$^{18}$F]fluoride anions; and
   (b) contacting said solid stationary phase with a non-aqueous solution comprising a precursor compound of formula (I):

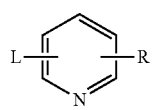
(I)

and a solvent selected from acetonitrile, tert-butanol, dimethylformamide, dimethylsulphoxide, dimethylacetamide, tetrahydrofuran, dioxan, 1,2-dimethoxyethane, sulpholane, N-methylpyrolidinone, or mixtures thereof, or an ionic liquid, optionally in the presence of an organic non-nucleophilic base, whereby to produce a radiofluorinated compound of formula (II):

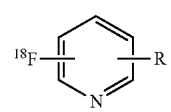
(II)

wherein: in formula (I), L is a positively charged leaving group; and in formulae (I) and (II), R is a group of the formula:

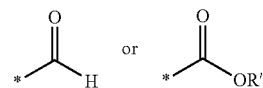

wherein R' is an electron-withdrawing group, wherein the radiofluorination process is performed at a temperature of from 10° C. to 25° C., and wherein the stationary phase is not contacted with a phase transfer catalyst during step (b).

2. The process of claim 1, wherein in step (b) the solid stationary phase is contacted with the non-aqueous solution of the precursor compound of formula (I) in the presence of an organic non-nucleophilic base.

3. The process of claim 1, wherein R is

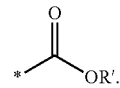

4. The process of claim 3, wherein R' is —CF$_3$, —CH$_2$CF$_3$, —CH(CF$_3$)$_2$, —C(CF$_3$)$_3$, or

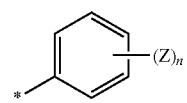

where n is an integer from 1 to 5 and each Z is independently —F, —Cl, —NO$_2$, or —CN.

5. The process of claim 1, wherein R is

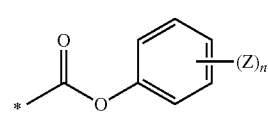

wherein n is an integer from 1 to 5 and each Z is independently —F, -Cl, —NO$_2$, or —CN. CN.

6. The process of claim 1, wherein the precursor compound of formula (I) is a compound of formula ($I^{tt}$):

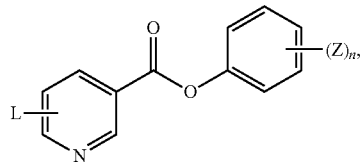

wherein L is a positively charged leaving group, n is an integer from 1 to 5 and each Z is independently—F, —Cl, —$NO_2$, or —CN.

7. The process of claim 1, wherein the precursor compound of formula (I) is a compound of general formula (P):

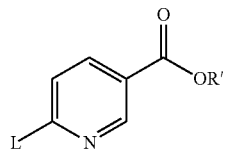

and wherein L and R' in said compound of general formula ($I^s$) are selected such that said precursor compound is one of compounds (1) to (21):

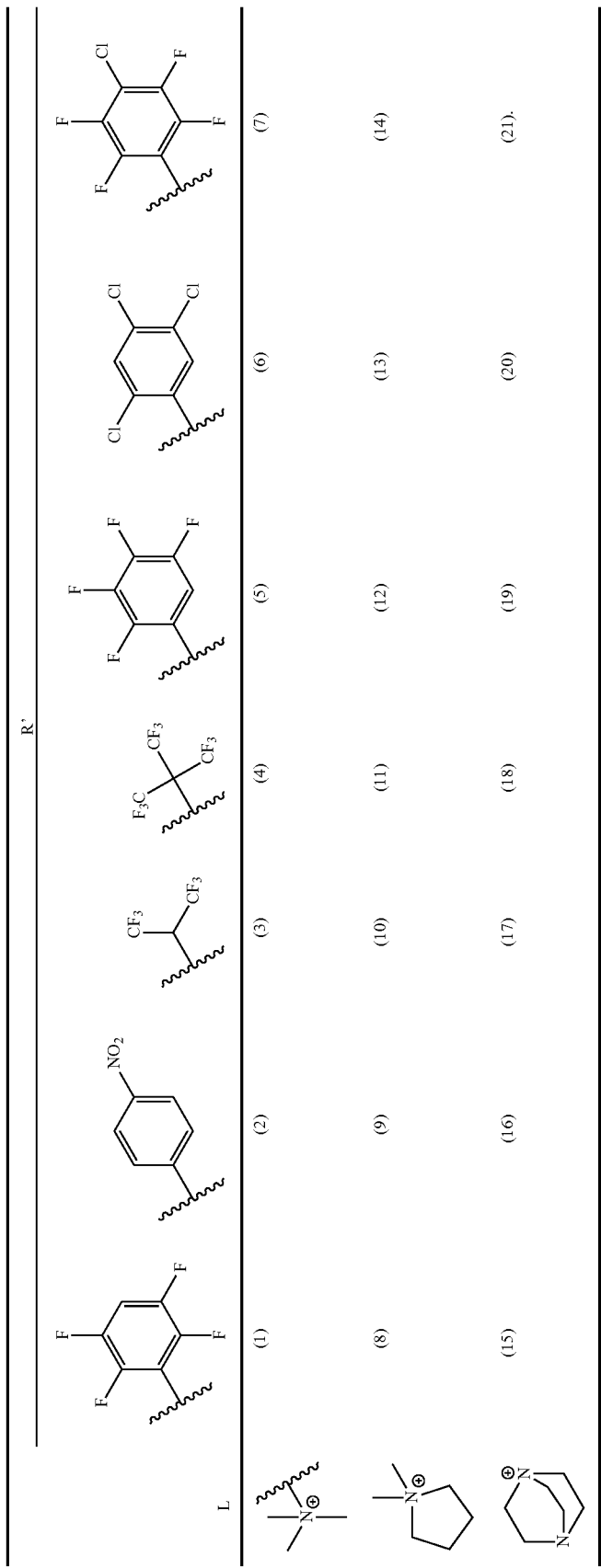

8. The process of claim 1, wherein R is

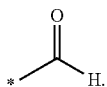

9. The process of claim 1, wherein the precursor compound of formula (I) is in the form of a trifluoromethanesulphonate salt.

10. The process of claim 1, further comprising reacting the compound of formula (II) with a compound of formula (III):

$$\text{H}_2\text{N-biomolecule} \tag{III}$$

to give a radiolabelled biomolecule of formula (IV):

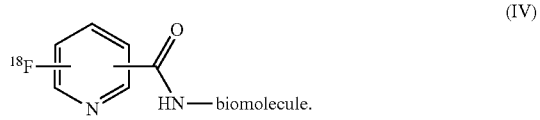

11. The process of claim 10, wherein the biomolecule is a peptide, protein, hormone, oligonucleotide, or antibody fragment.

12. The process of claim 10, wherein the biomolecule is a peptide selected from somatostatin analogues, bombesin, vasoactive intestinal peptide, chemotactic peptide analogues, α-melanocyte stimulating hormone, urea-based PSMA inhibitors, neurotensin, Arg-Gly-Asp peptide and its analogues, human pro-insulin connecting peptide, endothelin, angiotensin and formyl-norleucyl-leucyl-phenylalanyl-norleucyl-tyrosyl-lysine.

13. The process of claim 10, wherein the biomolecule comprises the fragment:

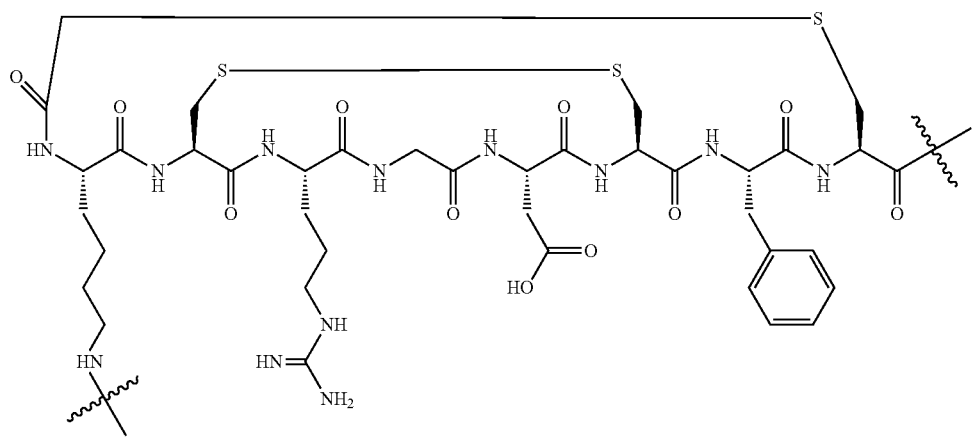

14. The process of claim 10, wherein the biomolecule is a peptide of formula (V):

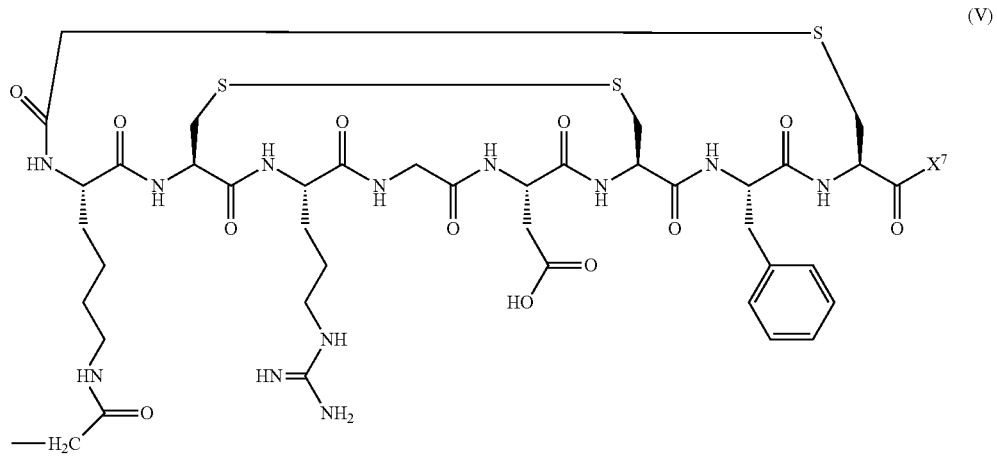

wherein $X^7$ is either —$NH_2$ or
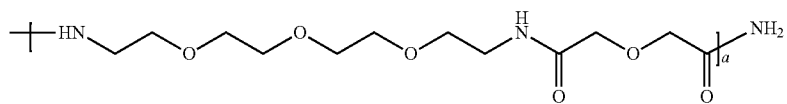
wherein a is an integer of from 1 to 10.
15. The process of claim 10, wherein the biomolecule is an aminooxy- or hydrazine-modified peptide.
16. The process of claim 10, wherein the biomolecule is
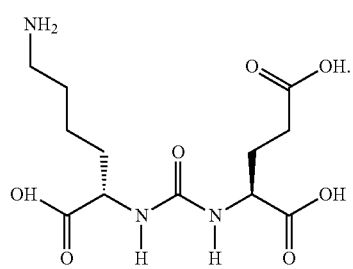 [SMILES: NCCCC[C@H](NC(=O)N[C@@H](CCC(=O)O)C(=O)O)C(=O)O]
* * * * *